(12) United States Patent
Akahori et al.

(10) Patent No.: US 7,141,755 B2
(45) Date of Patent: Nov. 28, 2006

(54) ACCELERATED WEATHERING TEST METHOD

(75) Inventors: Masahiko Akahori, Hyogo (JP); Tetsurou Kajino, Hyogo (JP); Minoru Umino, Chiba (JP); Harunori Gouji, Osaka (JP); Rie Tomita, Osaka (JP); Yasuhiro Shibata, Osaka (JP)

(73) Assignee: Nippon Paint Co., Ltd., Osaka (JP)

( * ) Notice: Subject to any disclaimer, the term of this patent is extended or adjusted under 35 U.S.C. 154(b) by 108 days.

(21) Appl. No.: 10/505,892

(22) PCT Filed: Feb. 26, 2003

(86) PCT No.: PCT/JP03/02104

§ 371 (c)(1),
(2), (4) Date: Nov. 22, 2004

(87) PCT Pub. No.: WO03/073074

PCT Pub. Date: Sep. 4, 2003

(65) Prior Publication Data

US 2005/0115931 A1    Jun. 2, 2005

(30) Foreign Application Priority Data

Feb. 27, 2002  (JP) .............................. 2002-051434
Oct. 29, 2002  (JP) .............................. 2002-314728
Nov. 14, 2002  (JP) .............................. 2002-331065

(51) Int. Cl.
*B23K 10/00* (2006.01)

(52) U.S. Cl. .......................... 219/121.36; 219/121.41; 219/121.44; 219/121.59; 156/345.26

(58) Field of Classification Search ........... 219/121.43, 219/121.59, 121.36, 121.4, 121.44, 121.48; 456/345.29, 345.26
See application file for complete search history.

(56) References Cited

FOREIGN PATENT DOCUMENTS

| JP | 9-178727 A | 7/1997 |
|---|---|---|
| JP | 2001-59809 A | 3/2001 |
| JP | 2001-208675 A | 8/2001 |
| JP | 2003-139682 A | 5/2003 |

OTHER PUBLICATIONS

Teion Plasma o Riyo shita Netsu Koka-gata Acryl Jushikei no Rekka Sokushin to Taikyusei Hyoka (Accelerated degradation of a thermosetting acrylic resin film by using the low temperature-plasma and evaluation for durability of the film), *Japan Society of Colour Material*, pp. 98-99, Oct. 25, 1996.

*Primary Examiner*—Mark Paschall
(74) *Attorney, Agent, or Firm*—Connolly, Bove, Lodge & Hutz, LLP

(57) ABSTRACT

The present invention provides an accelerated weathering test method, which gives the results having a high correlation with the results of natural exposure and can significantly reduce a test duration.

An accelerated weathering test method for a coating film with a remote plasma apparatus, wherein it is possible to bring the interior of the remote plasma apparatus into a reduced pressure and introduce gas, for example oxygen gas, into the apparatus.

18 Claims, 20 Drawing Sheets

Top view

Side view

ACCELERATED WEATHERING TEST METHOD

TECHNICAL FIELD

The present invention relates to an accelerated weathering test method, particularly an accelerated weathering test method in which a remote plasma apparatus is used.

BACKGROUND ART

As for walls of residential houses and buildings and bodies of automobiles, coating films are often formed on their surfaces in order to protect their appearances or provide glories. Such the coating films are degraded gradually due to the effects of sun light, water, changes in ambient temperature or the like during exposure to the outdoors for long time and their appearances deteriorate.

The degradation of the coating film is generally evaluated as weather resistance. This evaluation of the weather resistance is conducted by exposing the coating films in Okinawa in Japan or Florida in USA. In these areas, it is hot and wet and an amount of ultraviolet light is much, and the environment is harsh for coating films. Since such exposure requires much time, various accelerated weathering testers have been developed as an apparatus capable of evaluating weather resistance in a short time.

However, in the previous accelerated weathering testers, some coating films, which were considered to have adequate weather resistance by a test, actually caused problems such as cracks or discoloration with time and its correlation with the results of actual exposure was not insufficient. And, the test in which the conventional accelerated weathering testers are used has an acceleration factor of about 10 to 100 times, and an accelerated weathering tester, which can conduct the test at higher acceleration factor, has been desired.

On the other hand, in a conventional accelerated weathering tester, loads applied to coating films for the accelerated degradation are limited to factors such as ultraviolet light, water and changes in ambient temperature, given from nature, and there were few attempts to apply another factors.

In Japanese Kokai Publication Hei-9-178727, there is disclosed a test method of organic materials, an accelerated degradation of coating films is conducted using a plasma generating apparatus of a type having parallel plate type electrodes in this patent. However, there is no clear description on a correlation with the results of natural exposure. Further, in the case where a coating film is formed on a metal material, when plasma is irradiated directly to the coating film using such an apparatus, a metal portion must be masked because spark-discharge may be generated to destroy the material, and in addition it is difficult to keep a constant test conditions because the temperature of the coating film is raised due to the occurrence of induction heating by a high-frequency. On the other hand, in the case where a coating film is formed on a porous inorganic material such as a ceramic board, there was a problem that a volatile ingredient from the inorganic material had an effect on test results in a high-vacuum condition in which plasma is irradiated.

When in order to resolve such the problems, the present inventors studied the results of natural exposure tests in detail, it was recognized that the degradation of coating films in natural exposure proceeded based on the degradation of the surface layer in the surface of a coating film. On the contrary, in the conventional accelerated weathering tester, it became apparent that the degradation of a deep layer simultaneously occurs. It is supposed that an adequate correlation with the results of the natural exposure cannot be obtained due to such the different points.

If a usual plasma generating apparatus, which is described in Japanese Kokai Publication Hei-9-178727, is employed, it is impossible to selectively develop only the degradation of the surface layer and to resolve the problems described above.

SUMMARY OF THE INVENTION

In view of the above state of the art, it is an object of the first present invention to provide an accelerated weathering test method, which gives the results having a high correlation with the results of a natural exposure and can significantly reduce a test duration.

In view of the above state of the art, it is another object of the second present invention to provide an accelerated weathering test method, which gives the results having a high correlation with the results of a natural exposure by selectively developing degradation from the surface of a coating film.

The first present invention is an accelerated weathering test method of accelerating the degradation of the surface of an article to be treated by irradiating plasma to said article to be treated, wherein said plasma is generated by a remote plasma apparatus.

The above-mentioned article to be treated is preferably one having a surface on which a coating film is formed. In the present invention, the interior of the above-mentioned remote plasma apparatus is preferably brought into a reduced pressure. And, in the present invention, gas is preferably introduced into the above-mentioned remote plasma apparatus. The above-mentioned gas is preferably an oxygen gas.

The second present invention is accelerated weathering test method of accelerating the degradation of the surface of an article to be treated by irradiating an oxygen atom converted to a radical to said article to be treated, wherein said irradiation is conducted under the conditions of a degree of vacuum of 0.4 to 10 torr and an oxygen flow rate of 50 to 500 ml/min.

The above-mentioned oxygen atom converted to a radical is preferably generated by a remote plasma apparatus using a power source of 20 to 200 W. The above-mentioned accelerated weathering test method is preferably a method of developing selectively the degradation of the surface layer of the article to be treated. In the present invention, a filter is installed between a plasma generation section and a radical irradiation section in order to selectively irradiate the oxygen atom converted to a radical from the remote plasma apparatus. The above-mentioned article to be treated is preferably one having a surface on which a coating film is formed.

| EXPLANATION OF THE NUMERICAL SYMBOLS | |
|---|---|
| 1 | plasma generation section |
| 2 | high-frequency power source |
| 3 | sample stage |
| 4 | vacuum pump |
| 5 | flow of gas |
| 6 | flow of neutral plasma |
| 7 | plasma irradiation section |
| 8 | remote plasma apparatus |
| 9 | tube |
| 10 | direction of current |
| 11 | filter |

DETAILED DESCRIPTION OF THE INVENTION

Hereinafter, the present invention will be described in detail.

A remote plasma apparatus used in the first present invention is provided with a mechanism generating plasma persistently independent of a sample stage on which an article to be treated is placed, and a mechanism which can control a density of a neutral radical entering the article to be treated to any value by means of power applied to its electrodes. While a plasma generation section and a plasma irradiation section are located extremely close to each other in a usual plasma apparatus, the plasma generation section and the plasma irradiation section are located at a distance from each other in the above-mentioned remote plasma apparatus. Though its distance varies depending on an output of a power source to be used or required energy of plasma, when a high-frequency power source of, for example, about 200 W is used, it is preferably several tens of cm and more preferably 20 to 60 cm. Since the plasma generation section and the plasma irradiation section are located at a distance from each other as mentioned above, an electron or an ion is deactivated before being irradiated and a neutral radical can be selectively irradiated to the article to be treated.

A power source in the above-mentioned plasma generating apparatus is not particularly limited and for example, a high-frequency (generally, 13.56 MHz) and a microwave (generally, 2450 MHz) can be employed. When plasma by the above-mentioned high-frequency is used, an output thereof is preferably 20 to 200 W.

Figure 1:
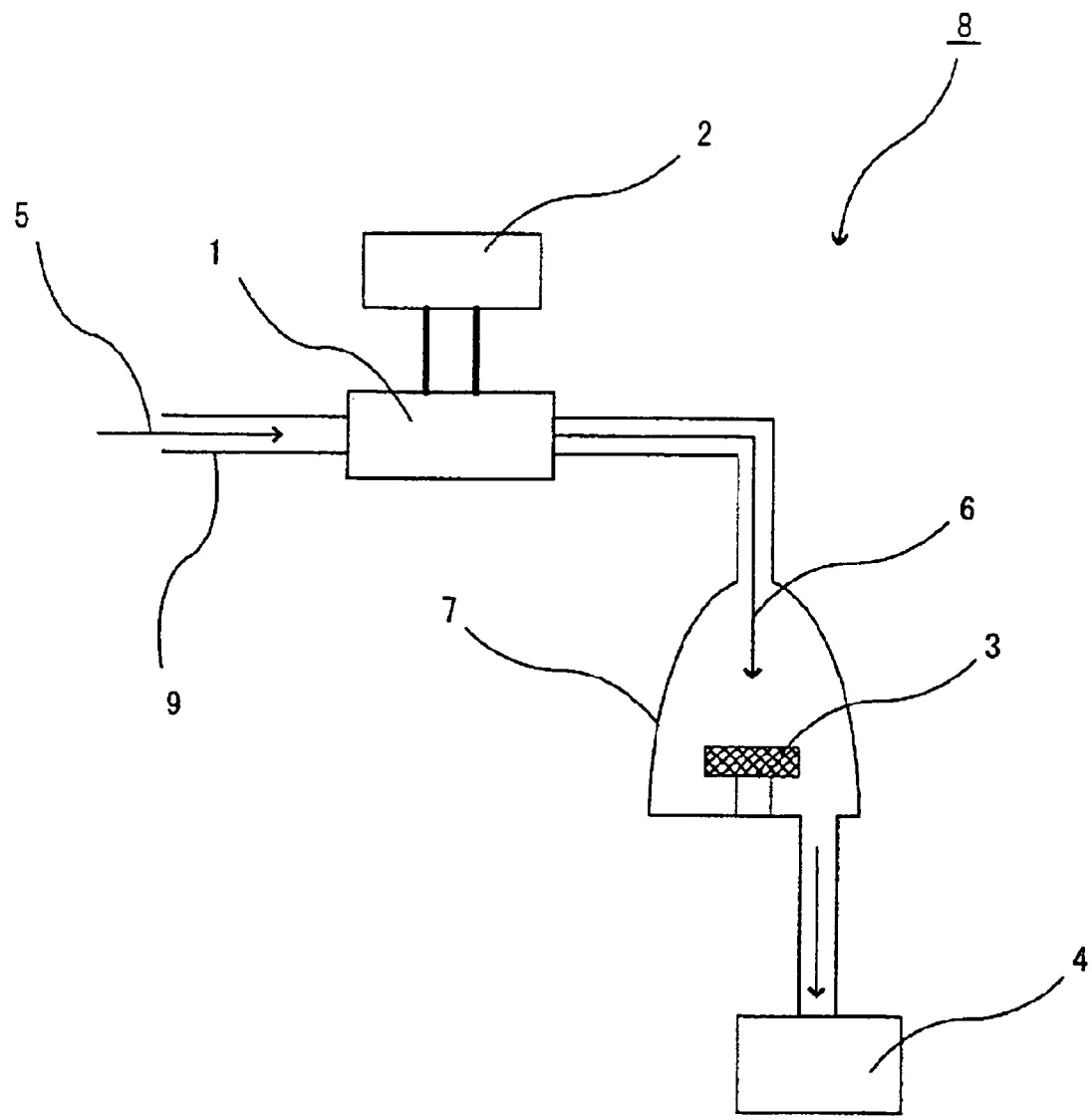
FIG. 1 is a view representing an example of a remote plasma apparatus used in the present invention.

FIG. 1 shows an example of the above-mentioned remote plasma apparatus. The remote plasma apparatus 8 includes the plasma generation section 1 and the plasma irradiation section 7 located at a distance from each other. The apparatus has the means for adjusting this distance from 20 to 60 cm. In addition, the distance between the plasma generation section 1 and the plasma irradiation section 7 described here refers to a distance between the plasma generation section 1 and a sample stage 3, which is movable up and down, installed in the plasma irradiation section 7. A high-frequency power source 2 is connected to the plasma generation section 1 as a power source, and therefore a density of a neutral radical entering the article to be treated can be controlled to any value. And, a tube 9 for introducing gas is connected to the plasma generation section 1. On the other hand, a vacuum pump 4 is connected to the plasma irradiation section 7 and therefore an interior of the remote plasma apparatus 8 can be brought into a reduced pressure.

An article to be treated in the accelerated weathering test method of the present invention, is not particularly limited, but usually substances comprising organic materials, the surfaces of which are degraded with time, are applied. As such the organic material, there are given various substrates such as metal materials, plastics, inorganic materials and woods having a coating film formed from a paint and a coating material on the surfaces thereof, in addition to substances composed of only an organic material such as plastic moldings or films. This coating film may be a free film. In the accelerated weathering test method of the present invention, since a remote plasma apparatus is used, there is no effect on a test resulting from the species of a substrate on which a coating film is formed and the flexibility of selecting the substrate is higher than a method described in Japanese Kokai Publication Hei-9-178727.

In the accelerated weathering test method of the present invention, first, an article to be treated, having a size adapted to the above-mentioned plasma irradiation section of the remote plasma apparatus, is placed on a sample stage as a sample. Then, the interior of the apparatus is brought into a reduced pressure. Its degree of vacuum is preferably adjusted so as to be about 0.1 torr to 5.0 torr. After making sure that the interior of the apparatus has been brought into a reduced pressure, treatment can be conducted by generating plasma. By introducing gas into the apparatus in this step, radical can be generated with efficiency. That is, in FIG. 1 previously described, after a vacuum pump 4 is started to bring the interior of the apparatus 8 into a reduced pressure, gas is introduced in the direction of the arrow 5 through a tube 9, and finally neutral plasma is irradiated in the direction of the arrow 6 to the sample on the sample stage 3.

As the gas of a radical source, there can be used, for example, oxygen, argon, helium and monomers having a double bond, but oxygen is desired in consideration of bringing the gas into correspondence with a degradation factor in the natural exposure and an alteration of the radical after the plasma irradiation. The above-mentioned gas is introduced into the apparatus, for example, at a flow rate of 100 to 300 ml/min, and the degree of vacuum in the apparatus is preferably adjusted so as to be about 0.75 torr or lower.

In the accelerated weathering test method of the present invention, a plasma irradiation time, which will be a test time, can be arbitrarily set. As a method of finding a time interval, which is proper as an irradiation time, there can be given, for example, a method of conducting irradiation for a given length of time and finding a required irradiation time in view of the results of the test. And, as another method, there may be employed a method in which a criterion is set for gloss retention and/or color difference of the coating film, and the gloss retention and/or color difference of a sample after a lapse of a certain test time is measured and the accelerated weathering test is continued until the measurements become below this criterion. In the accelerated weathering test method of the present invention, since it is possible to conduct a treatment in an extremely short time in comparison with a method using the conventional acceleration apparatus, the above-mentioned test time may be appropriately selected so as to be, for example, several hours or less in consideration of a sample.

A degree of degradation of the surface of the article to be treated, which has been treated by the accelerated weathering test method of the present invention, can be determined by visually evaluating an appearance and in addition to this, by measuring the gloss retention and the color difference in the case where a coating film is formed on the surface of the article to be treated.

The accelerated weathering test method of the present invention gives the results having a higher correlation with the results of an actual exposure compared with a method using the conventional accelerated weathering tester. This became apparent from measurements of secular changes of the above-mentioned gloss retention and color difference of the coating film. That is, when the treatment for degradation according to the natural exposure and the accelerated weathering test method of the present invention was applied to two or more species of coating films and the above-mentioned secular changes of the gloss retention and color difference was compared with one another, the correlations, which had not been found in the conventional accelerated weathering test method, were found.

On the other hand, the present inventors have newly found that the gloss retention is in correlation with the color difference in the natural exposure. And, this correlation was also identified in the accelerated weathering test method of the present invention. On the contrary, in the conventional accelerated weathering tester, the correlation between the gloss retention and the color difference was not found, and therefore this is considered to suggest, but not directly, that the accelerated weathering test method of the present invention gives the results having a higher correlation with the results of an actual exposure As the reason for the above results, because it is supposed to occur a degradation reaction mainly based on a radical reaction, in the surface of a coating film, in the accelerated weathering test method using the remote plasma apparatus of the present invention, it is supposed that likewise in the natural exposure, a degradation reaction due to a radical reaction may take place predominantly.

And, in the remote plasma apparatus used in the present invention, there is no fear of a temperature rise due to spark discharge or induction heating by high-frequency even in the case where a coating film is formed on a metal material since the plasma generation section and the plasma irradiation section are located at a distance from each other. And, if a volatile ingredient is generated from a porous inorganic material, there is little effect on the test results since particularly active ion species or electrons are not present in the plasma irradiation section.

Further, the above-mentioned remote plasma apparatus is also excellent in that it is possible to conduct a treatment in an extremely short time. The reason for this is assumed that while in a conventional accelerated tester utilizing a photochemical reaction, energy, which is given to the surface of an article to be treated, is about 1 eV, energy of active species in the above remote plasma apparatus is 10 to 100 eV.

An accelerated weathering test method of the second present invention is a method of developing selectively only degradation from the surface layer of the article to be treated by selectively irradiating the neutral oxygen radical to the surface of the article to be treated and can perform stably an accelerated weathering test which gives the results having a high correlation with the results of natural exposure.

Figure 2:
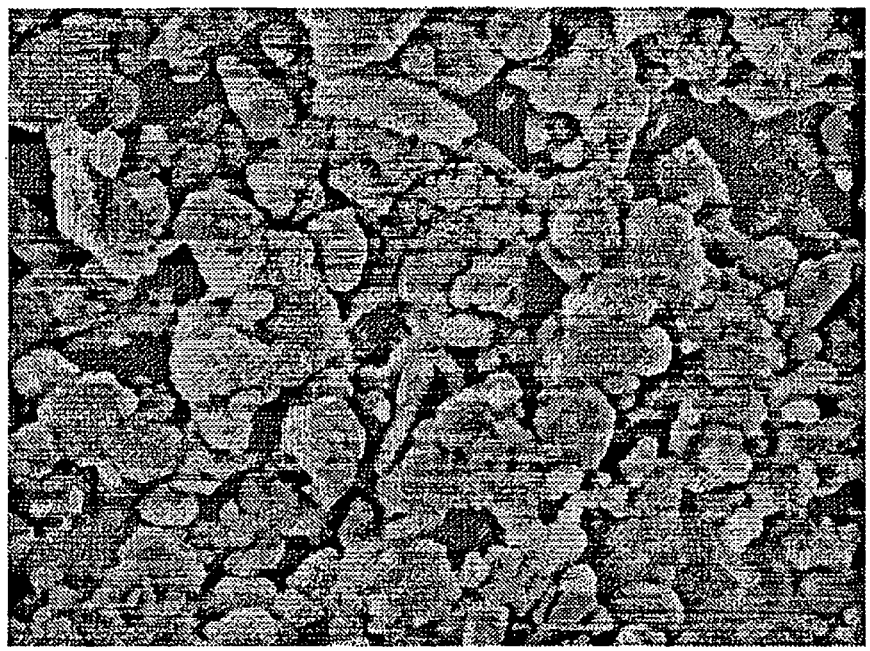
FIG. 2 shows an electron microscope photograph of the surface of a coating film after a coating film degradation test by natural exposure was conducted on a coating film of a sample used in Example during five years.
Figure 3:
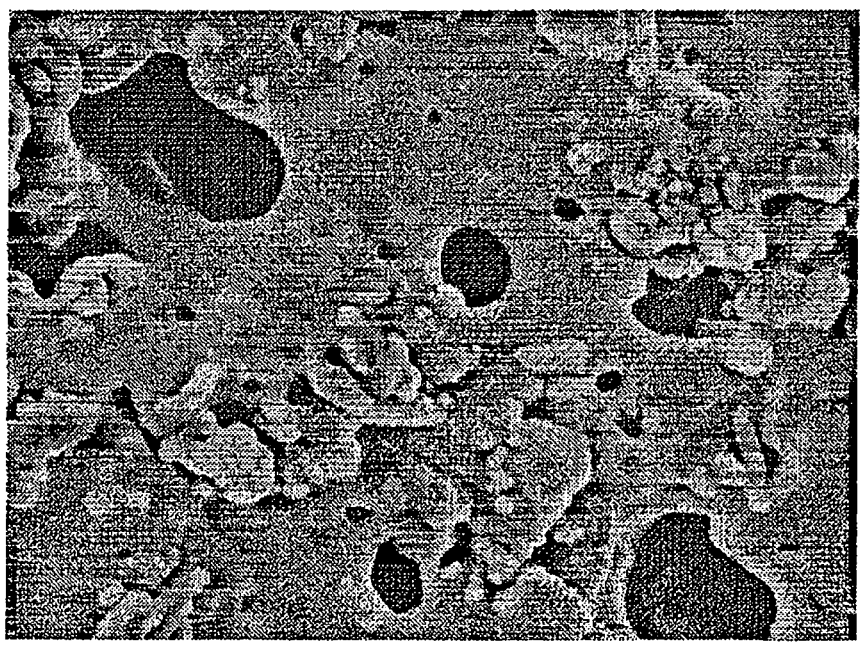
FIG. 3 shows an electron microscope photograph of the surface of a coating film after a coating film degradation test with an accelerated weathering tester of the metal halide lamp type, manufactured by DAIPLA WINTES CO., LTD. was conducted on a coating film of a sample used in Example.

The results of natural exposure tests of coating films and the test results of coating films according to a conventional accelerated weathering test method were investigated in detail, so that some distinctive points became clear. One of them is that in the natural exposure test, pigment particles were exposed to the surface (refer to FIG. 2). From this, it is thought that the degradation of a coating film is predominantly caused by the degradation of the surface in which resin in the surface is lost by natural exposure test. On the other hand, in a degraded coating film treated according to tests using a conventional accelerated test apparatus, for example, a lamp type emphasizing a short wavelength, pinholes having a diameter of 1 μm or less exist in the coating film (refer to FIG. 3), and it is supposed that the degradation of a deep layer is simultaneously developed. It is thought that the natural exposure test and the test using the conventional accelerated test apparatus are different in a mechanism of degradation from each other like this and this point is considered as one of the causes of the fact that the results of the conventional accelerated weathering test did not have an adequate correlation with the results of the natural exposure.

The reason for the occurrence of such a difference is assumed that when the accelerated degradation is conducted using strong ultraviolet light with a short wavelength as with a test using the conventional accelerated degradation tester, a degradation factor cannot stay in the surface of an article to be treated and the degradation is also accelerated inside the article to be treated, but in a mild degradation condition of nature, a degradation factor has an effect on only the surface of the article to be treated and the degradation of the surface layer predominantly occurs.

As another one of such a different point between the natural exposure test and the test using the conventional accelerated test apparatus, there can also be given a relationship between an amount of titanium oxide in the coating film and color difference. As a result of measuring color difference in conducting the natural exposure tests on three species of coating films differing in an amount of titanium oxide, respectively, over 5 years, it was found that the color difference, namely, the degradation of coating film increased as the content titanium oxide in the coating film increased (refer to FIG. 4). It is supposed that this result reflects the fact that in the degradation of the coating film in the natural exposure, an effect of a photocatalyst reaction by titanium oxide is large. That is, it is supposed that in natural conditions, titanium oxide in the vicinity of the surface layer is activated by ultraviolet light irradiated, and a photocatalyst reaction occurs and thereby, the degradation of coating films mainly based on the degradation of the surface occurs.

Figure 4:
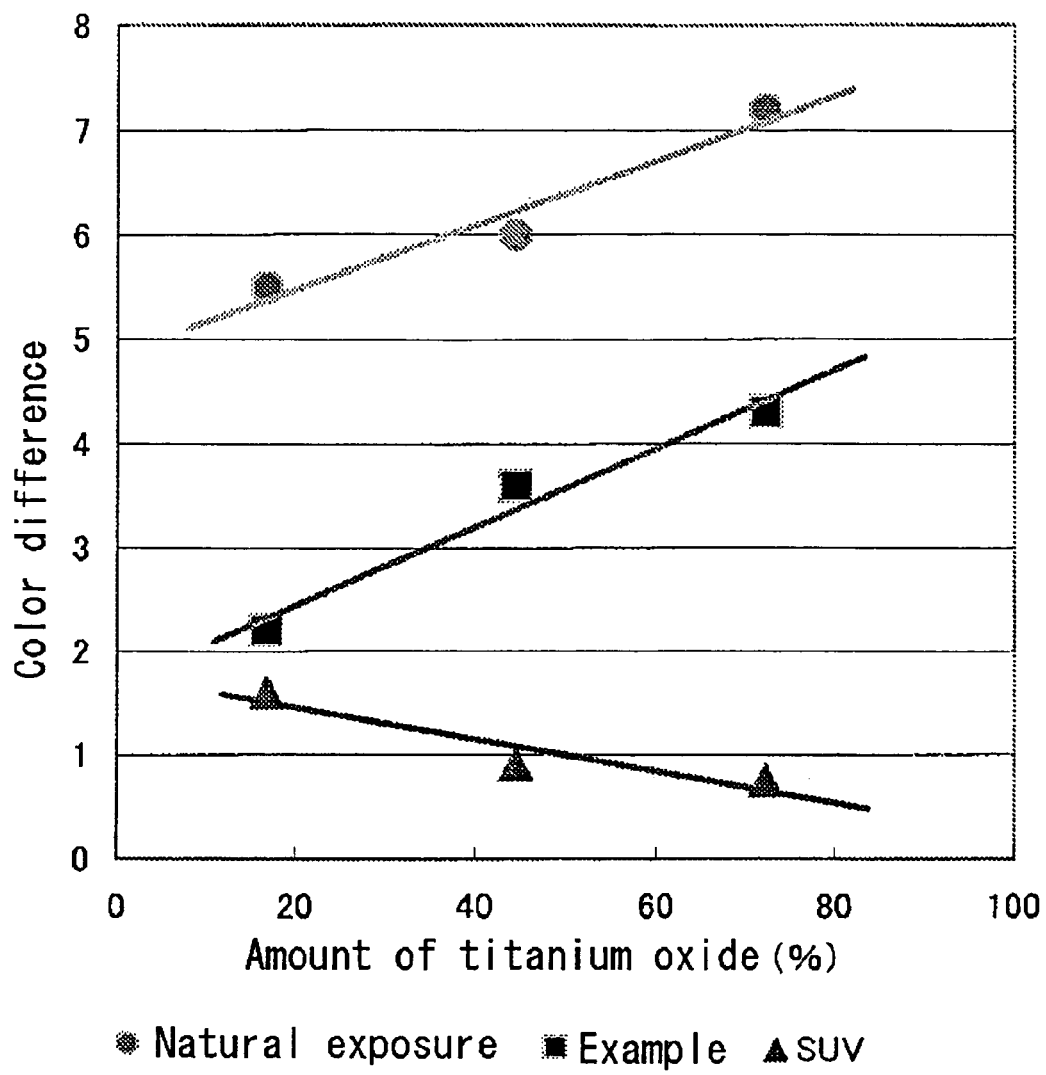
FIG. 4 is a view showing a relationship between an amount of titanium oxide in a coating film to be treated and color difference after degradation.

On the contrary, when light was irradiated to the same coating films with an accelerated weathering tester of the metal halide lamp type, an conventional accelerated weathering tester, the color difference decreased as the content of titanium oxide increased, resulting in a smaller degradation of coating films (refer to FIG. 4). Such the test results were opposed to that of the natural exposure test. The reason why the opposed result was obtained is assumed that in the accelerated weathering test using the accelerated weathering tester of the metal halide lamp type, the irradiation of strong ultraviolet light causes not only the degradation of the surface layer due to titanium oxide but also the degradation of the deep layer. That is, when an amount of titanium oxide in the coating film is increased, masking capability of titanium oxide significantly blocks the penetration of ultraviolet light into an inside of the coating films. Therefore, it is supposed that the degradation of the deep layer is significantly blocked through blocking of ultraviolet light, and consequently the result that the coating film becomes resistant to the degradation as an amount of titanium oxide increases is obtained. In the conventional accelerated weathering tester causing such a difference, it is difficult to predict adequately the degradation of a coating film.

Based on the viewpoint described above, it was found that if it is possible to conduct such an accelerated degradation test that the degradation of the surface layer is predominant, it is possible to provide an accelerated test method which gives the results having a high correlation with the results of natural exposure and can measure a lifetime of the article to be treated more exactly. The present invention has been made based on such findings, and can repeat the degradation in the surface of the coating film, which is similar to a mechanism of the degradation from the surface (the degradation of surface layer) occurred in the natural exposure, using the remote plasma apparatus by selectively irradiating the radical to the article to be treated under the specified conditions.

In the accelerated weathering test method of the present invention, the degradation of the surface of the article to be treated is accelerated by irradiating an oxygen atom converted to a radical to the article to be treated. That is, when the accelerated degradation is conducted according to the method described in Japanese Kokai Publication Hei-9-178727, not only radical species but also electrons and ions are irradiated to the surface of the article to be treated and a thermal factor is promoted to cause the surface temperature to increase significantly, and therefore such a method cannot give a sufficient correlation with the results of natural exposure. But, when the selective accelerated degradation is performed with radical species, the degradation of surface layer is selectively developed, and therefore an accelerated degradation test, the results of which have a high correlation with the results of natural exposure, can be conducted. And, since among radical species, the oxygen atom converted to a radical is relatively stable, it is easy to handle and an accelerated degradation test using it can be conducted efficiently.

In the present invention, it is necessary to limit the degree of vacuum and the oxygen flow rate in the irradiation within a proper range. By limiting these conditions, it is possible to develop the degradation of the surface with efficiency due to an oxygen atom converted to a radical and an accelerated weathering test in an environment closer to natural exposure can be conducted.

The above-mentioned degree of vacuum must be within a range of 0.4 torr (lower limit) to 10 torr (upper limit). The above degree of vacuum refers to a degree of vacuum in a state of conducting the accelerated weathering test of the present invention, namely, a degree of vacuum in a state in which plasma is generated using a power source of 20 to 200 W and an oxygen gas is introduced into the interior of the remote plasma apparatus at a flow rate of 50 to 500 ml/min. When the degree of vacuum is in a high vacuum of less than 0.4 torr, the degradation is accelerated extremely fast since the oxygen atom converted to a radical is stable, so that measurement error tends to occur and a good accelerated degradation of the coating film cannot be performed. When it is more than 10 torr, the control of conditions becomes difficult since the plasma becomes unstable. The above lower limit is more preferably 0.6 torr, furthermore preferably 1.0 torr. The above upper limit is more preferably 5 torr, furthermore preferably 2 torr.

As the gas of a radical source, an oxygen gas is used. The above-mentioned oxygen gas is introduced into the apparatus at a flow rate of 50 to 500 ml/min, and thereby, the degree of vacuum in the apparatus is preferably adjusted so as to be about 1.0 torr or lower. When the flow rate of the oxygen gas is less than 50 ml/min, an absolute amount of oxygen molecules in plasma is small, and therefore a problem arises that oxygen molecules energized by electron are insufficient and consequently an amount of neutral radical to be generated is reduced. When it is more than 500 ml/min, an exhaust amount of a vacuum pump increases and consequently a problem arises that a flow velocity of oxygen gas increases and therefore an amount of radical reaching an article to be coated increases, so that the control of conditions becomes difficult.

In order to generate the above-mentioned oxygen atom converted to a radical with efficiency, a remote plasma apparatus may be used. As the above remote plasma apparatus, there can be given an apparatus which is provided with a mechanism generating plasma persistently independent of a sample stage on which an article to be treated is placed, and a mechanism which can control a density of a neutral radical entering the article to be treated to any value by means of power applied to its electrodes.

A power source in the above plasma generating apparatus is not particularly limited and for example, a high-frequency (generally, 13.56 MHz) and a microwave (generally, 2450 MHz) can be employed. An output at the above-mentioned power source is 20 to 200 W. When the output is less than 20 W, it becomes necessary to place the article to be treated close to the plasma generating apparatus because of a low output and it becomes difficult to selectively treat with only radical. And, when it is more than 200 W, ions or electrons also reach the article to be coated because of a too high output and the article to be coated is heated, and therefore it is impossible to conduct selective treatment from the surface.

Further, when a temperature of the article to be coated is elevated, a correlation with the results of the natural exposure becomes low since a degradation factor due to thermal degradation will have an effect. Particularly when a temperature of the article to be treated exceeds 50° C., reduction in the correlation is remarkable due to the fact that this condition significantly deviates from the actual natural phenomena (ambient temperature) and an effect of the thermal behavior of polymeric resin becomes large, and therefore it is preferred to remain the temperature of the article to be treated below 40° C. by establishing the above-mentioned conditions.

Figure 5:
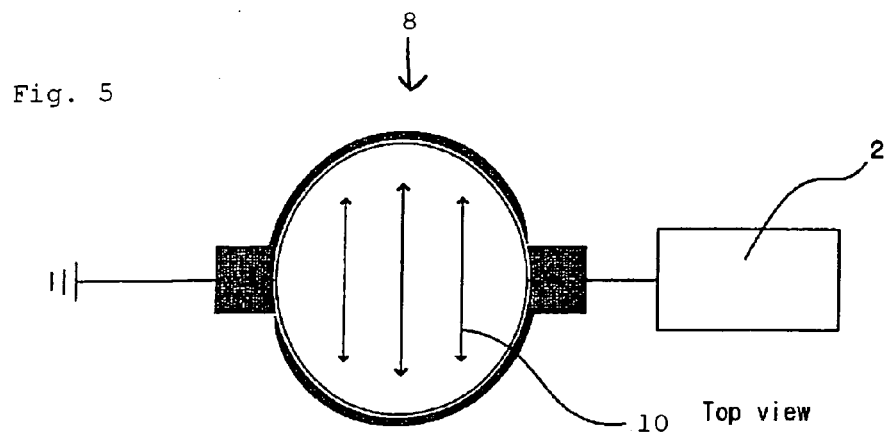
FIG. 5 is a view representing an example of a remote plasma apparatus used in the present invention.
Figure 5:
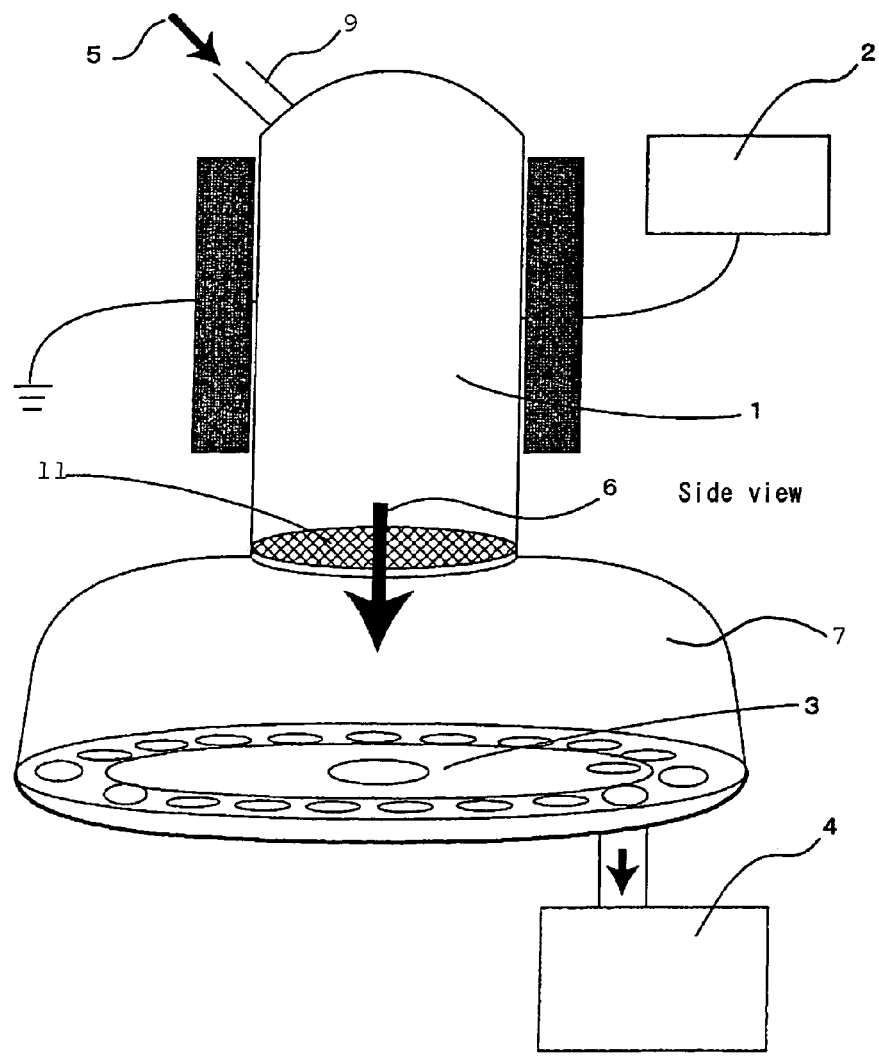

FIG. 5 shows an example of a remote plasma apparatus which can be used in the present invention. The remote plasma apparatus 8 includes the plasma generation section 1 and the plasma irradiation section 7 located at a distance from each other. This distance may be adjusted to 15 to 60 cm. It is possible to selectively advance the degradation of the surface layer by adjusting this distance for an optimum in response to an output of a power source. In addition, the irradiation distance described here refers to a distance between the plasma generation section 1 and a sample stage 3 to which a radical is irradiated. A high-frequency power source 2 is connected to the plasma generation section 1 as a power source, and therefore a density of a neutral radical entering the article to be treated can be controlled to any value. And, a tube 9 is connected to the upper end of the plasma generation section 1. On the other hand, a vacuum pump 4 is connected to the sample stage 3 and therefore an interior of the apparatus can be brought into a reduced pressure.

A filter 11 may be installed between the plasma generation section and the plasma irradiation section. The above-mentioned filter is a conductor having many holes provided along the direction of progress of particles. By trapping particles bearing electrical charges such as electrons and ions with the conductor, only radical species selectively passes through the filter, and therefore only radical species converted to a radical can be irradiated to the article to be treated. By grounding the filter, it is possible to release the charged electricity out of the apparatus.

An article to be treated in the accelerated weathering test method of the present invention, is not particularly limited, but usually substances comprising organic materials, the surfaces of which are degraded with time, are applied. As such the organic material, there are given various substrates such as metal materials, plastics, inorganic materials and woods having a coating film formed from a paint and a coating material on the surfaces thereof, in addition to substances composed of only an organic material such as plastic moldings or films. This coating film may be a free film. In the accelerated weathering test method of the present invention, since a remote plasma apparatus is used, there is no effect on a test resulting from the species of a substrate on which a coating film is formed and the flexibility of selecting the substrate is higher than a method described in Japanese Kokai Publication Hei-9-178727.

In the accelerated weathering test method of the present invention, first, an article to be treated, having a size adapted to the above-mentioned plasma irradiation section of the remote plasma apparatus, is placed on a sample stage as a sample. Then, the interior of the apparatus is brought into a reduced pressure. By introducing an oxygen gas into the apparatus at a flow rate of 50 to 500 ml/min after making sure that the interior of the apparatus has been brought into a reduced pressure and adjusting the degree of vacuum in the apparatus in a state of flowing the oxygen gas so as to be 0.4 torr to 10 torr, it is possible to generate plasma with efficiency to conduct treatment. That is, in FIG. 4 previously described, after a vacuum pump 5 is started to bring the interior of the apparatus 8 into a reduced pressure, gas is introduced in the direction of the arrow 5, and finally neutral plasma is irradiated in the direction of the arrow 6 to the sample on the sample stage 3.

In the accelerated weathering test method of the present invention, a radical irradiation time, which will be a test time, can be arbitrarily set. However, since when the article to be treated is treated for an excessively long time, it rises in temperature and factors of thermal degradation have effects on the degradation of the article to be treated, it is preferred to treat it within a range that temperature differentials of the article to be treated is 3° C. or less before and after irradiation.

A degree of degradation of the surface of the article to be treated, which has been treated by the accelerated weathering test method of the present invention, can be determined by visually evaluating an appearance and in addition to this, by measuring the gloss retention and the color difference in the case where a coating film is formed on the surface of the article to be treated.

The accelerated weathering test method of the present invention gives the results having a higher correlation with the results of an actual exposure compared with a method using the conventional accelerated weathering tester. This became apparent from measurements of a relationship between an amount of titanium oxide and the degradation of coating films. That is, when the degradation of coating films according to the accelerated weathering test method of the present invention was developed on two or more species of coating films varying in an amount of titanium oxide, a result that the degradation of coating films is accelerated as the amount of titanium oxide increases was obtained. Such a result is similar to the degradation of coating films due to the natural exposure.

As the reason why the above results were obtained, it is supposed that in the natural exposure, the degradation reaction from the surface due to a radical reaction predominantly takes place and supposed that in the present invention, since the oxygen atom converted to a radical is selectively irradiated, the degradation reaction from the surface due to a radical reaction predominantly takes place and therefore the results of the method of the present invention have a high correlation with the results of natural exposure.

The accelerated weathering test method of the present invention defines specified ranges of the output of the power source of the apparatus, the degree of vacuum inside the apparatus and the oxygen rate introduced. Thereby, the rise in surface temperature of the article to be treated is inhibited, so that the effect on the degradation of a coating film can be suppressed, and the amount of radical irradiation can be stabilized, so that the degradation from the surface of the article to be treated can be selectively developed in an accelerated weathering test. Accordingly, the accelerated weathering test method of the present invention is a test method which gives the results having a high correlation with the results of natural exposure.

BEST MODES FOR CARRYING OUT THE INVENTION

Hereinafter, the present invention will be described in more detail by way of examples, but the present invention is not limited to these examples.

Invention 1

(Preparation of Sample)

Each of aqueous acrylic emulsion coating compositions A, B and C having a PWC of 22%, which contains titanium oxide and barium sulfate in the proportions shown in the following Table 1 and was toned in ivory similarly, was applied to a flat board cut in a predetermined size, on which an under layer comprising an impregnated sealer and a permeance resistant sealer was formed, at a rate of 100 g/m$^2$ using a spray. This was set for 5 minutes and then dried at 100° C. for 5 minutes to obtain a sample A, B or C, being an article to be treated, on the surface of which a coating film is formed.

TABLE 1

|  | Coating compositions | | |
| --- | --- | --- | --- |
|  | A | B | C |
| Titanium oxide | 3 | 8 | 15 |
| Barium sulfate | 15 | 10 | 3 | unit: PWC %

(Outdoor Exposure Test)

Weathering test by outdoor exposure test was conducted on the above-mentioned samples A to C according to direct exposure tests (JIS Z 2381 General requirements for outdoor exposure test, and JIS K 5600-7-6) at the Okinawa No.2 exposure field of Nippon Paint Co., Ltd. during from September 1994 to September 1999. The location of the exposure field is as follows.

Location: about 26° 20' north latitude and about 127° 45' minutes east longitude Address: 373-309, Kadena-cho Aza Mizugama, Nakagami-gun, Okinawa prefecture In the above-mentioned test, measurement of gloss retention and color difference after lapses of one year, two years and five years was conducted as follows.

(Measurement of Gloss Retention and Color Difference)

The gloss value of the samples was measured at 60° incidence-reflex angle using micro-TRI-gloss, which is a gloss meter manufactured by BYK-Gardner, before and after the test. The gloss retention (GR; Gloss Retention) is obtained by multiplying the value obtained by dividing a gloss value measured after the test by a gloss value measured before the test by 100. On the other hand, the color difference ($\Delta E$) was measured with a calorimeter CR-300 manufactured by KONICA MINOLTA HOLDINGS, INC.

EXAMPLE 1

A sample was placed on a sample stage 3 in a remote plasma apparatus having a structure illustrated in FIG. 1, and an interior of the apparatus was brought into a reduced pressure of 0.5 torr by using a vacuum pump 4. Then, an oxygen gas was continued to be flown at a flow rate of 200 ml/min in the direction of the arrow 5. In this state, a degree of vacuum was 0.75 torr. While keeping a temperature of the sample stage at 30° C., plasma was generated by a high-frequency power source 2 using power of 50 W of high-frequency of 13.56 MHz and irradiated to the sample. The sample was taken out at time when 10 minutes had elapsed since the initiation of irradiation and the gloss retention (GR) and the color difference ($\Delta E$) were measured. After the measurement, the sample was replaced back into the remote plasma apparatus, and plasma irradiation was repeated in a manner similar to the case described above and the sample was measured. The total irradiation time was 50 minutes. A temperature rise of the sample was not particularly recognized during the test and the accelerated weathering test could be carried out without problems.

Comparative Example 1

(Accelerated Weathering Test Method with a Conventional Apparatus No. 1)

An accelerated weathering test was conducted on the above samples A to C referring to JIS K5400 9.8 (Accelerated weathering) using Daipla Metal Weather (hereinafter, referred to as DMW), which is an accelerated weathering tester of the metal halide lamp type, manufactured by DAIPLA WINTES CO., LTD. In the test, light irradiation of 4 hours was conducted using a light source of 60 mW/cm$^2$ under the conditions of temperature of 63° C. and humidity of 40%, and then after carrying out showering for 10 seconds, the samples were held for 4 hours under the wet conditions of temperature of 30° C. and humidity of 98%. This procedure was takes as one cycle and this cycle was repeated during a predetermined duration. In the test, the gloss retention (GR) and the color difference (ΔE) were measured after a lapse of specified time.

Comparative Example 2

(Accelerated Weathering Test Method with a Conventional Apparatus No. 2)

An accelerated weathering test was conducted on the above samples A to C referring to JIS B 7753 (sunshine carbon-arc type weathering test) and JIS K 5400 9.8 (Accelerated weathering) using Sunshine Weather Meter (hereinafter, referred to as SWM), which is an accelerated weathering tester of the sunshine carbon-arc type, manufactured by Suga Test Instruments Co., Ltd. In the test, light irradiation was conducted for a specified duration using a light source of 2 mW/cm$^2$ under the conditions of temperature of 63° C., humidity of 50% and continuous showering. In the test, the gloss retention (GR) and the color difference (ΔE) were measured after a lapse of specified time.

Comparative Example 3

(Accelerated Weathering Test Method with a Conventional Apparatus No. 3)

An accelerated weathering test was conducted on the above samples A to C referring to JIS K5400 9.8 (Accelerated weathering) using Super UV Tester (hereinafter, referred to as SUV), which is an accelerated weathering tester of the metal halide lamp type, manufactured by IWASAKI ELECTRIC Co., Ltd. In the test, light irradiation of 4 hours was conducted using a light source of 100 mW/cm$^2$ under the conditions of temperature of 63° C. and humidity of 40%, and then after carrying out showering for 10 seconds, the samples were held for 4 hours under the wet conditions of temperature of 30° C. and humidity of 98%. This procedure was takes as one cycle and this cycle was repeated during a predetermined duration. In the test, the gloss retention (GR) and the color difference (ΔE) were measured after a lapse of specified time.

(Secular Change of Gloss Retention and Color Difference)

Figure 6:
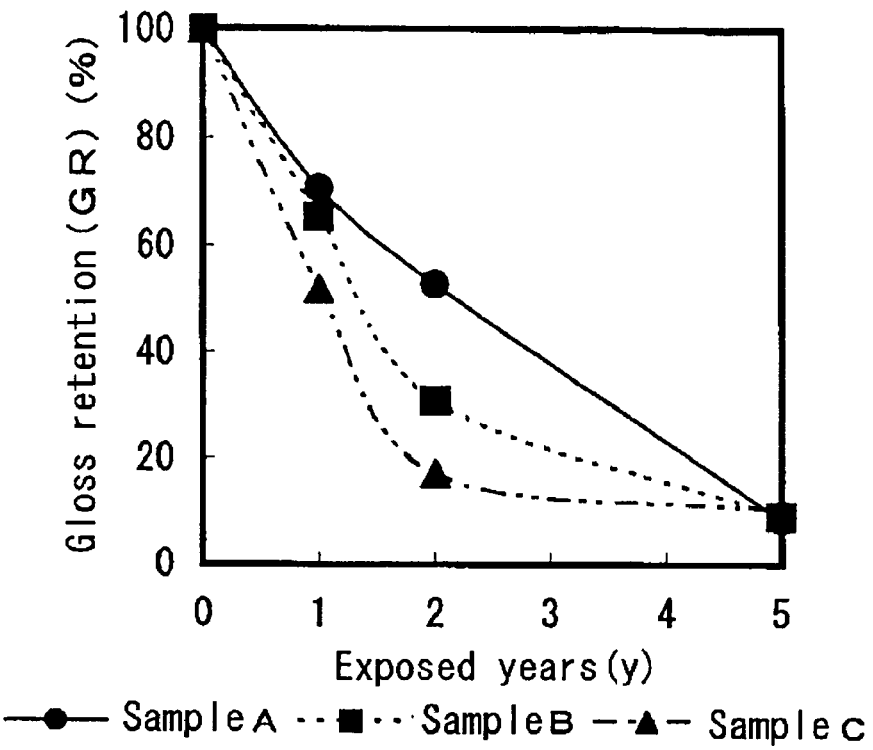
FIG. 6 is a view showing the secular change of gloss retention (GR) in conducting an outdoor exposure test on samples A to C.
Figure 7:
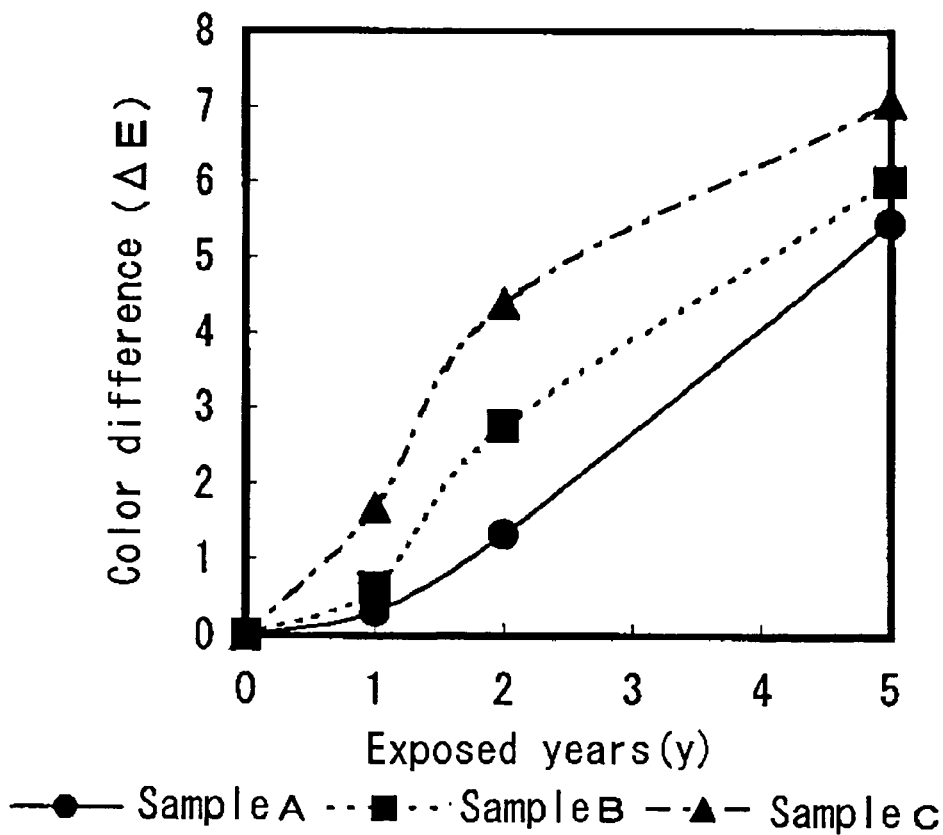
FIG. 7 is a view showing the secular change of color difference (ΔE) in conducting an outdoor exposure test on samples A to C.
Figure 8:
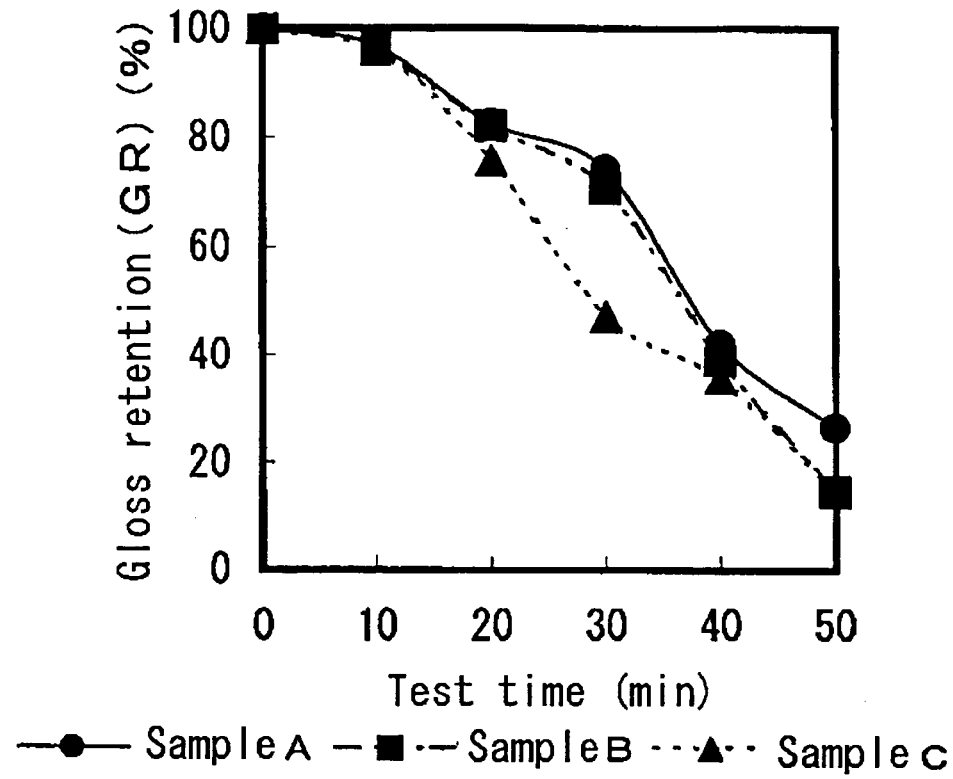
FIG. 8 is a view showing the secular change of gloss retention (GR) in conducting an accelerated weathering test according to Example on samples A to C.
Figure 9:
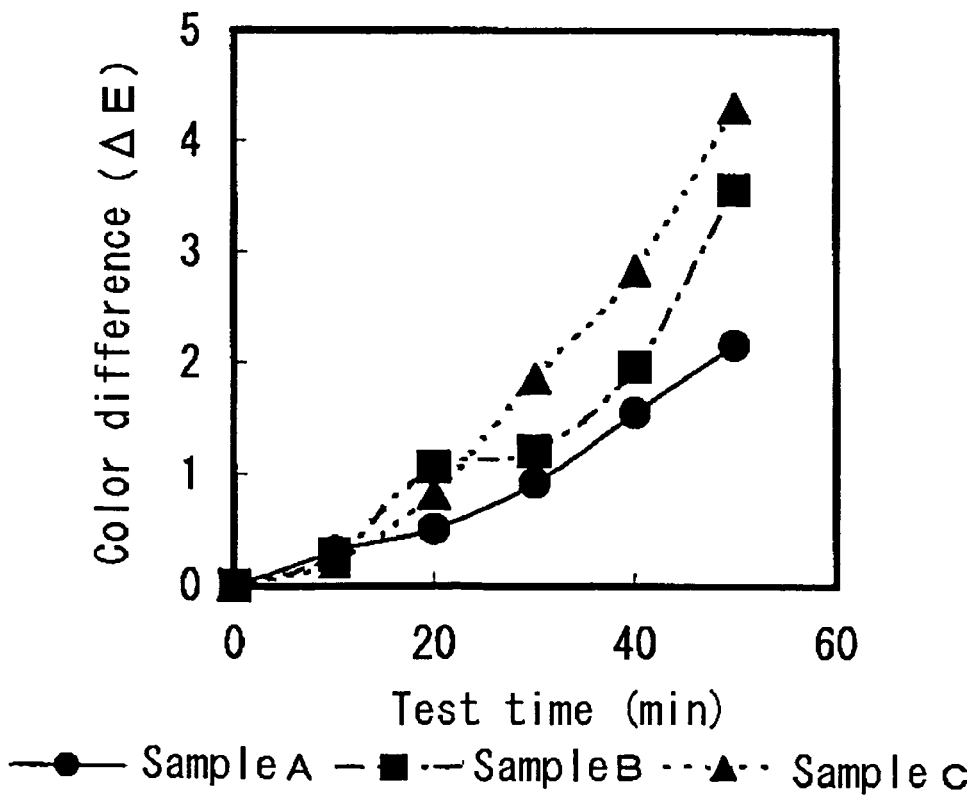
FIG. 9 is a view showing the secular change of color difference (ΔE) in conducting an accelerated weathering test according to Example on samples A to C.
Figure 10:
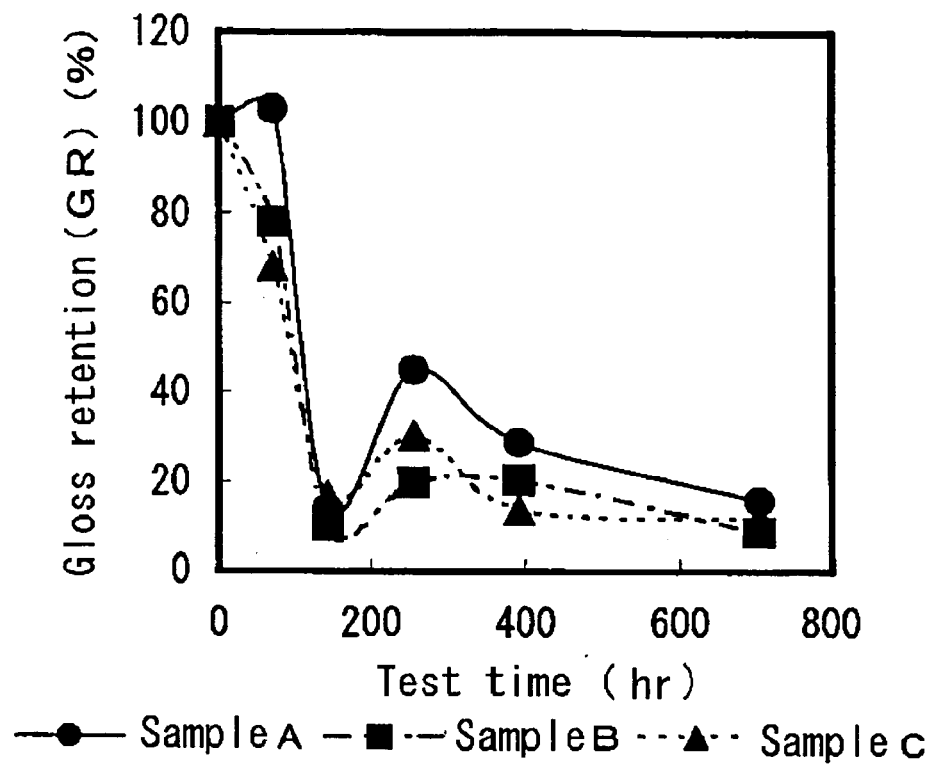
FIG. 10 is a view showing the secular change of gloss retention (GR) in conducting an accelerated weathering test according to Comparative Example 1 on samples A to C.
Figure 11:
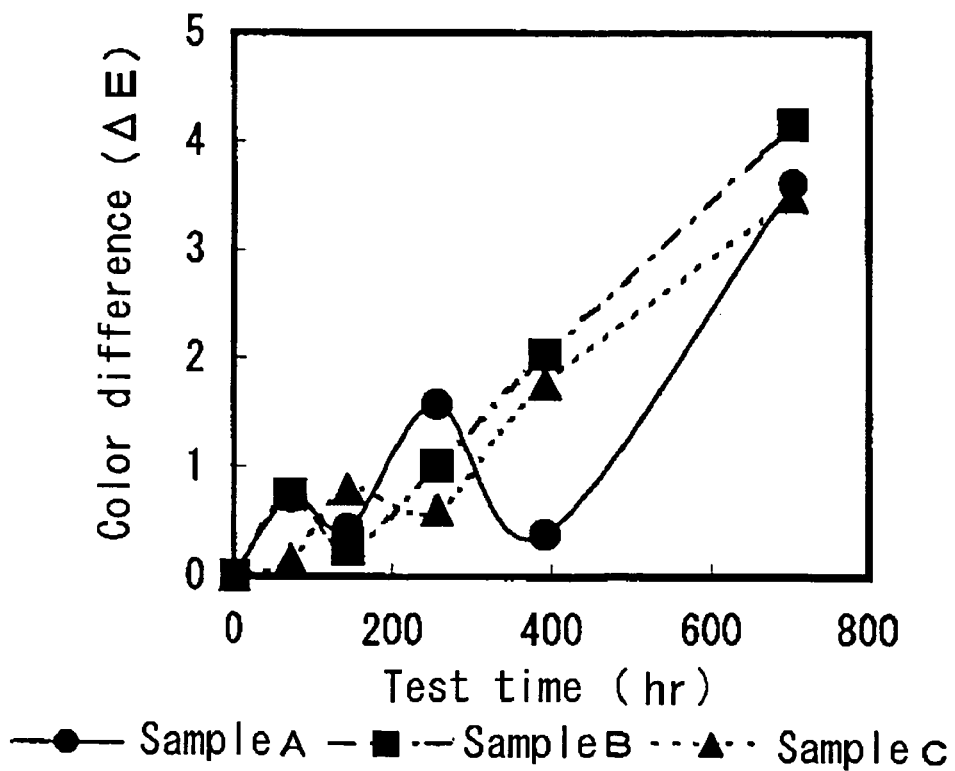
FIG. 11 is a view showing the secular change of color difference (ΔE) in conducting an accelerated weathering test according to Comparative Example 1 on samples A to C.
Figure 12:
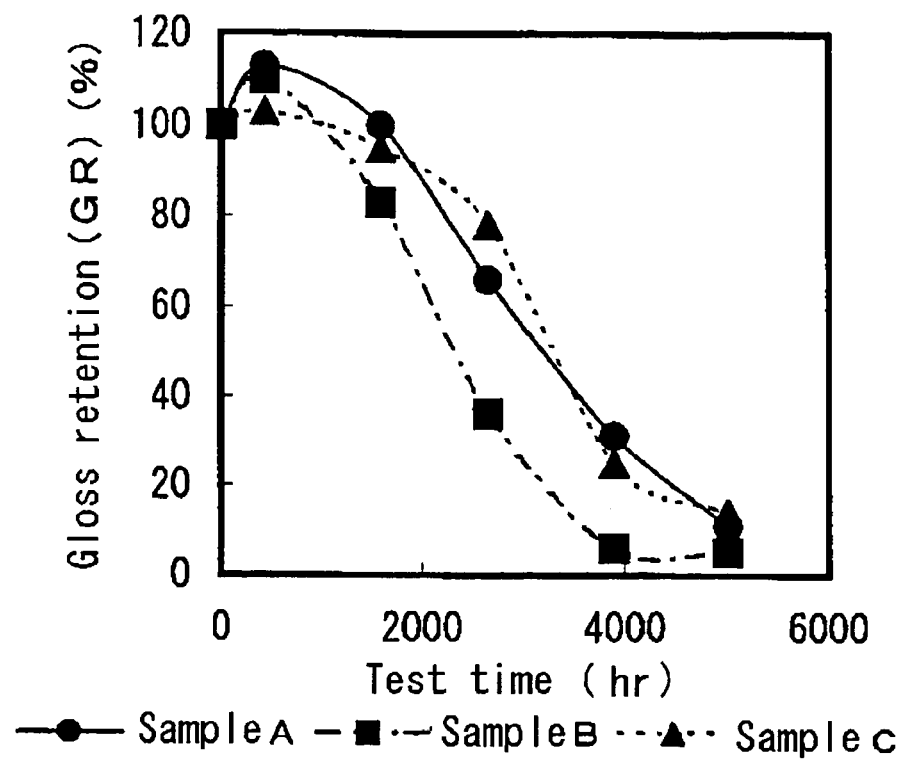
FIG. 12 is a view showing the secular change of gloss retention (GR) in conducting an accelerated weathering test according to Comparative Example 2 on samples A to C.
Figure 13:
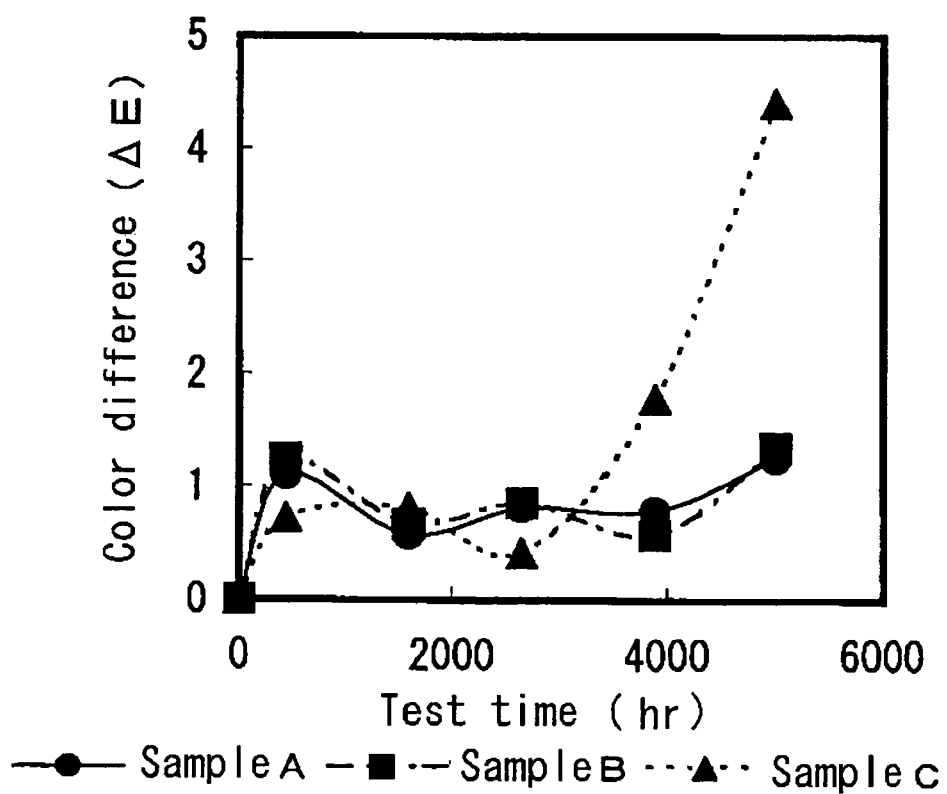
FIG. 13 is a view showing the secular change of color difference (ΔE) in conducting an accelerated weathering test according to Comparative Example 2 on samples A to C.
Figure 14:
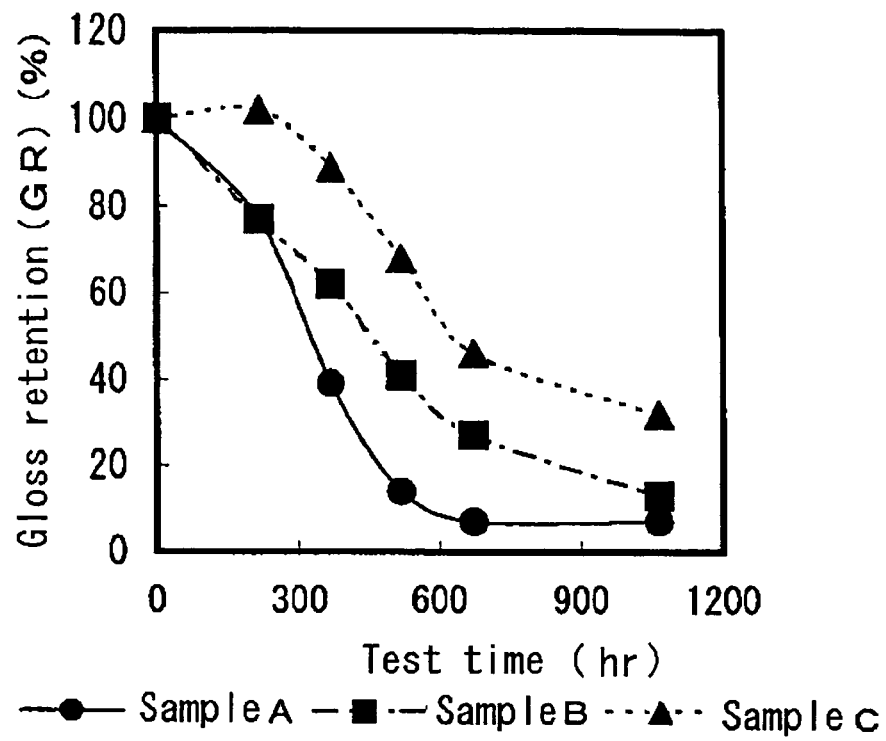
FIG. 14 is a view showing the secular change of gloss retention (GR) in conducting an accelerated weathering test according to Comparative Example 3 on samples A to C.
Figure 15:
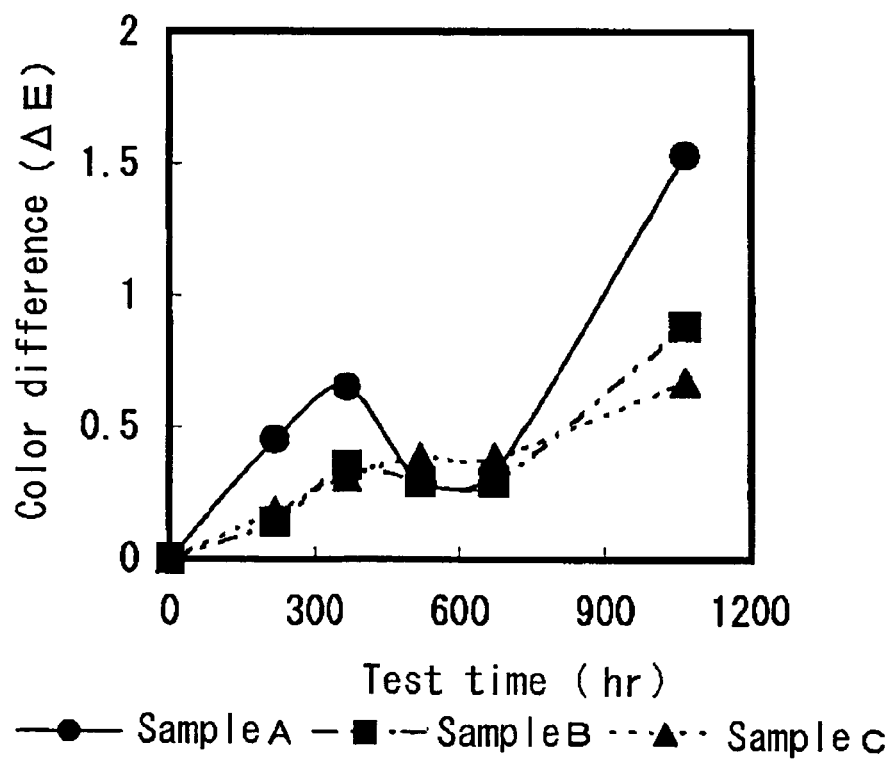
FIG. 15 is a view showing the secular change of color difference (ΔE) in conducting an accelerated weathering test according to Comparative Example 3 on samples A to C.

The respective graphs showing the secular change of the gloss retention (GR) and the color difference (ΔE) obtained by the above respective tests were shown in FIGS. 6 and 7 (Outdoor exposure tests), FIGS. 8 and 9 (Examples) and FIGS. 10 and 11 (Comparative Example 1), FIGS. 12 and 13 (Comparative Example 2), and FIGS. 14 and 15 (Comparative Example 3).

Viewing these graphs, it is verified that while the results of Example 1 of the present invention resemble Outdoor exposure tests in patterns of changes in the gloss retention and the color difference, the results of Comparative Example 1 are different in patterns of change in the gloss retention and the results of Comparative Example 2 are different in patterns of change in the color difference from Outdoor exposure tests, respectively.

(Endurance Time)

In the accelerated weathering test method, the instant when the gloss retention declined to 50% was considered to be as the instant when the coating film had been degraded, and the test time that elapses before the gloss retention declined to 50% was defined as an endurance time, the values were read out from FIGS. 6, 8, 10, 12 and 14. The results are shown in Table 2.

TABLE 2

|  | Outdoor Exposure Test (unit: year) | Example (unit: minute) | Comparative Example 1 (unit: hour) | Comparative Example 2 (unit: hour) | Comparative Example 3 (unit: hour) |
| --- | --- | --- | --- | --- | --- |
| Sample A | 2.2 | 38 | 100 | 3100 | 310 |
| Sample B | 1.3 | 37 | 110 | 2200 | 450 |
| Sample C | 1.0 | 33 | 90 | 3200 | 620 |

From Table 2, it is evident that the accelerated weathering test of Examples can reach the endurance time in shorter time than the accelerated weathering test of Comparative Examples 1 to 3 and can significantly reduce the time required for the tests.

And, in the outdoor exposure tests, decreasing order of the endurance time of respective samples is A, B, C. Since this result agrees with increasing order of an amount of titanium oxide, this result is considered to suggest that the degradation proceeds due to a photocatalyst reaction of titanium oxide in the surface of a coating film. The order of length of the above endurance time in the accelerated weathering tests of Examples is the same as outdoor exposure tests and it is thought that a degradation reaction similar to outdoor exposure tests occurs. On the contrary, in the accelerated weathering test of Comparative Examples, the above-mentioned relationship does not hold for any case, and there is a high probability that a different reaction occurs. From these results, it can be said that the accelerated weathering test method of the present invention gives the results having a higher correlation with the results of an outdoor exposure than the accelerated weathering test methods of Comparative Examples.

(Color Difference at a Maximum Endurance Time)

In the above outdoor exposure tests and the accelerated weathering tests, the endurance time of sample (for example, sample A in the case of outdoor exposure tests and Examples), of which the above endurance time is maximum, is defined as a maximum endurance time $T_L$ (for example, 2.2 years in the case of outdoor exposure tests), and the values of color difference $\Delta E_L$ of samples A to C at the above $T_L$ were read out from Figures. The results are shown in Table 3.

TABLE 3

| Outdoor Exposure Test | Example | Comparative Example 1 | Comparative Example 2 | Comparative Example 3 |
|---|---|---|---|---|
| Sample A | 1.5 | 1.4 | 0.7 | 0.8 | 0.6 |
| Sample B | 2.9 | 1.8 | 0.7 | 0.7 | 0.3 |
| Sample C | 4.5 | 2.6 | 0.4 | 0.8 | 0.3 |

In Outdoor exposure tests, the above $\Delta E_L$ is an indicator representing the degradation state of a coating film and $\Delta E_L$ takes smaller value as the weather resistance of a coating film becomes large. Therefore, the order of the weather resistance of three species of coating films is A, B, C in decreasing order from the results of Outdoor exposure tests. Only the results of the accelerated weathering tests of Examples exhibit the same order as the result of Outdoor exposure tests. The order of the values of the above $\Delta E_L$ in Comparative Examples is absolutely different from the result of Outdoor exposure tests. Accordingly, outdoor exposure test, namely, the weather resistance of an actual coating film cannot be predicted from the values of the $\Delta E_L$ in Comparative Examples, and on the contrary the weather resistance of an actual coating film can be predicted from the values of the $\Delta E_L$ in Examples.

(Relationship Between the Gloss Retention and the Color Difference)

Figure 16:
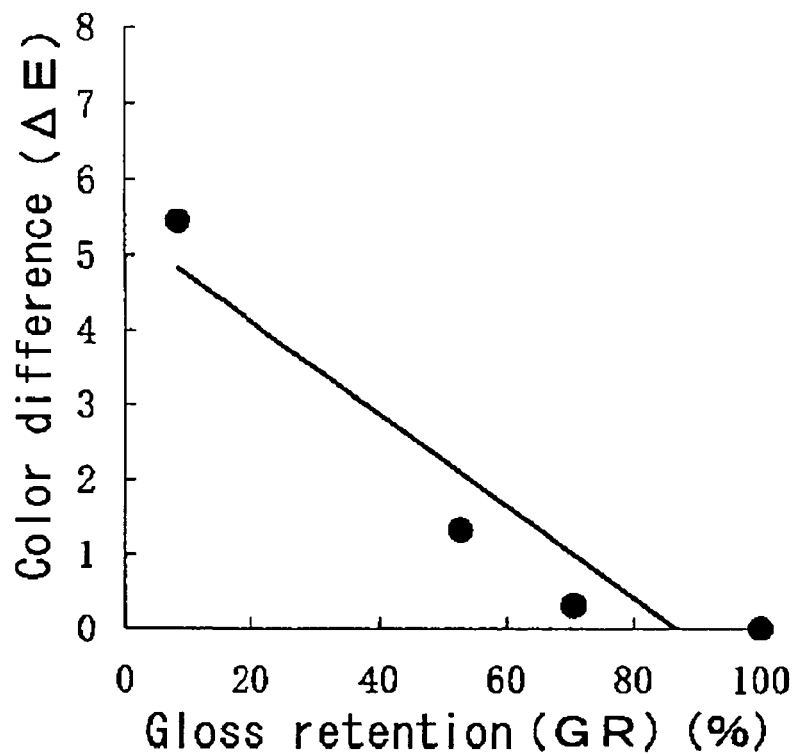
FIG. 16 is a view showing a relationship between gloss retention (GR) and color difference (ΔE) in conducting an outdoor exposure test on sample A.
Figure 17:
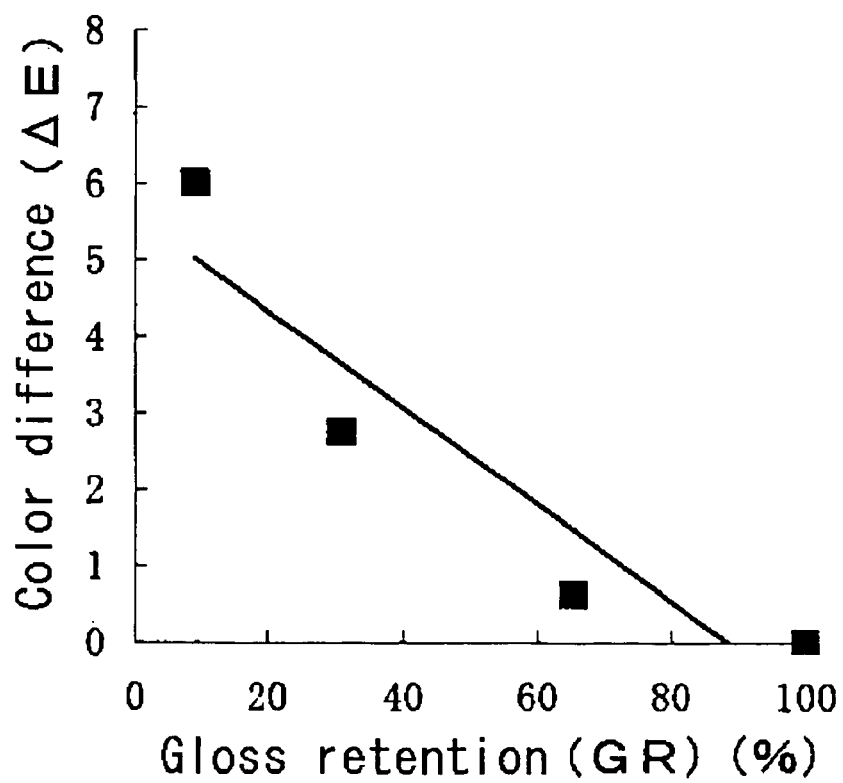
FIG. 17 is a view showing a relationship between gloss retention (GR) and color difference (ΔE) in conducting an outdoor exposure test on sample B.
Figure 18:
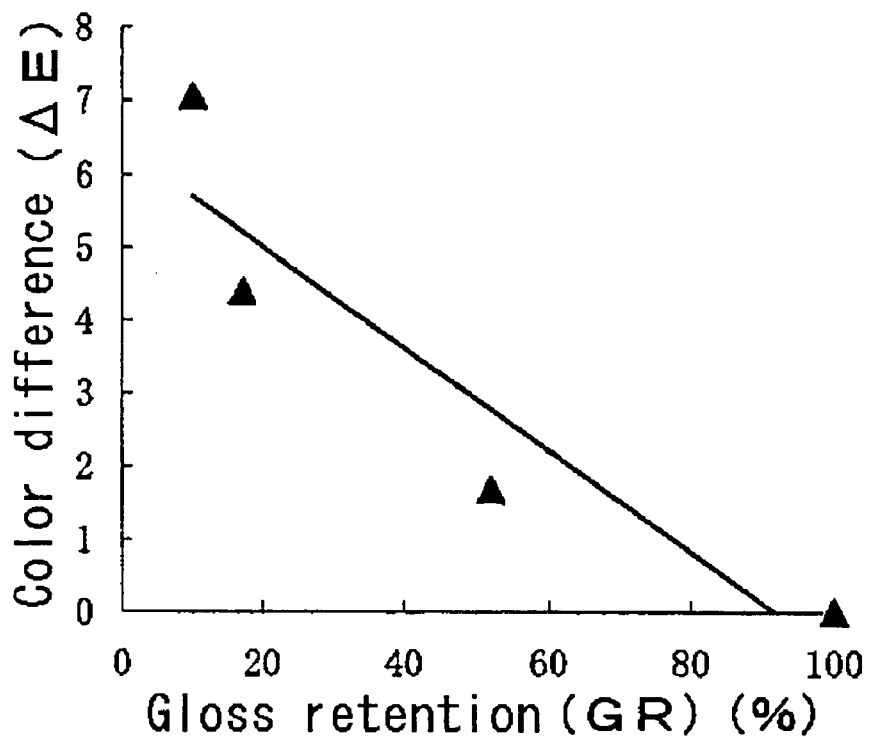
FIG. 18 is a view showing a relationship between gloss retention (GR) and color difference (ΔE) in conducting an outdoor exposure test on sample C.
Figure 19:
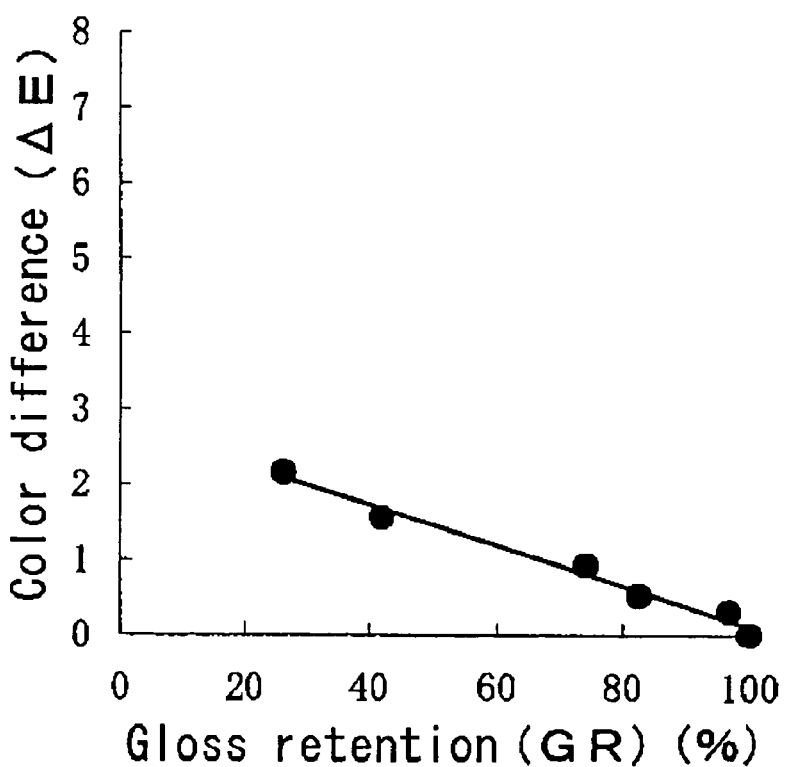
FIG. 19 is a view showing a relationship between gloss retention (GR) and color difference (ΔE) in conducting an accelerated weathering test according to Example on sample A.
Figure 20:
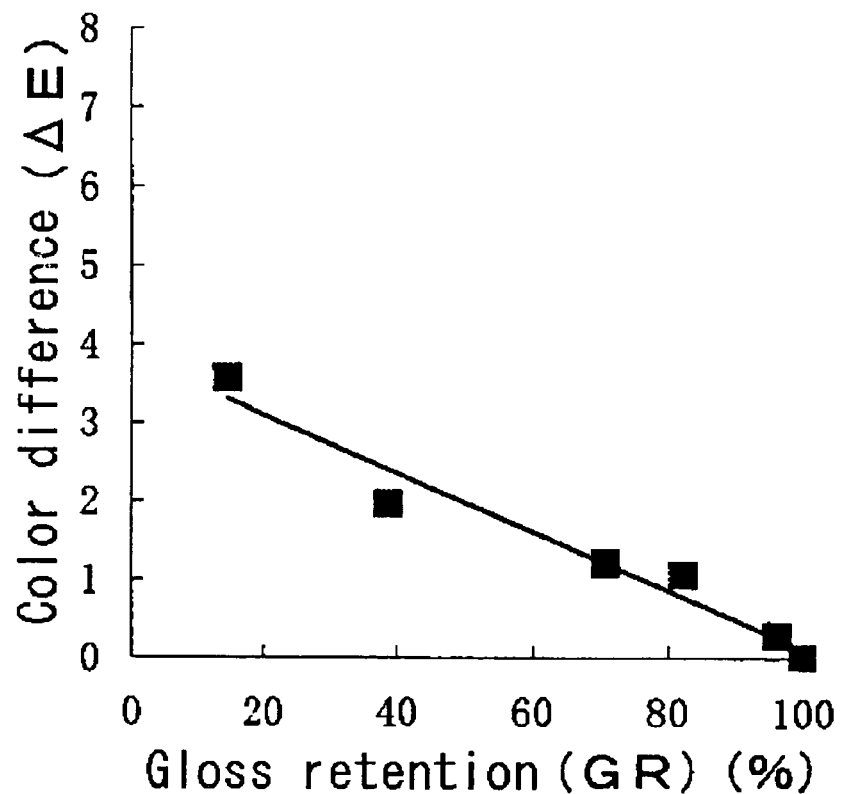
FIG. 20 is a view showing a relationship between gloss retention (GR) and color difference (ΔE) in conducting an accelerated weathering test according to Example on sample B.
Figure 21:
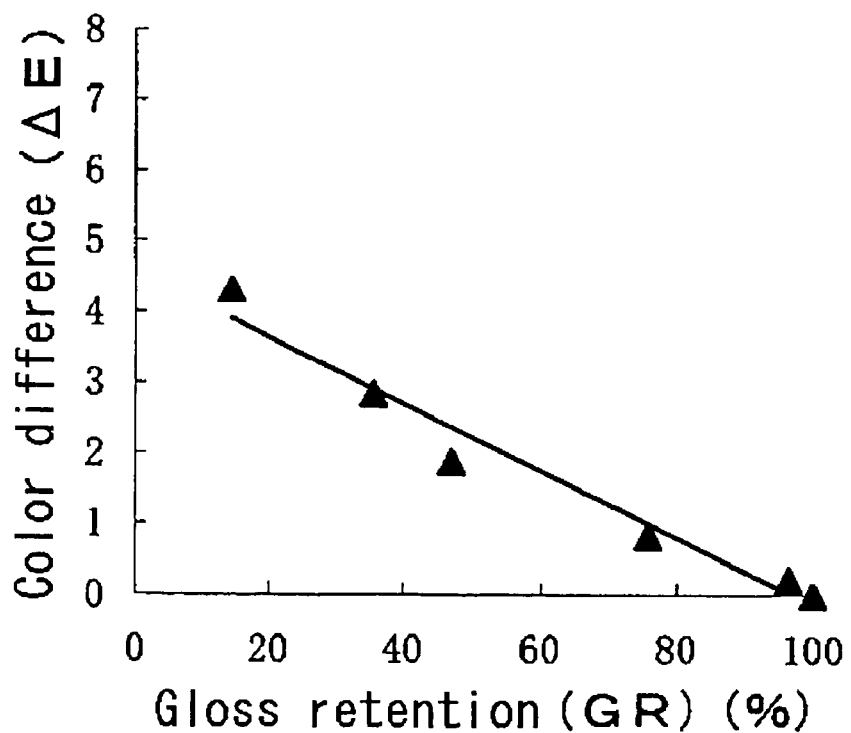
FIG. 21 is a view showing a relationship between gloss retention (GR) and color difference (ΔE) in conducting an accelerated weathering test according to Example on sample C.
Figure 22:
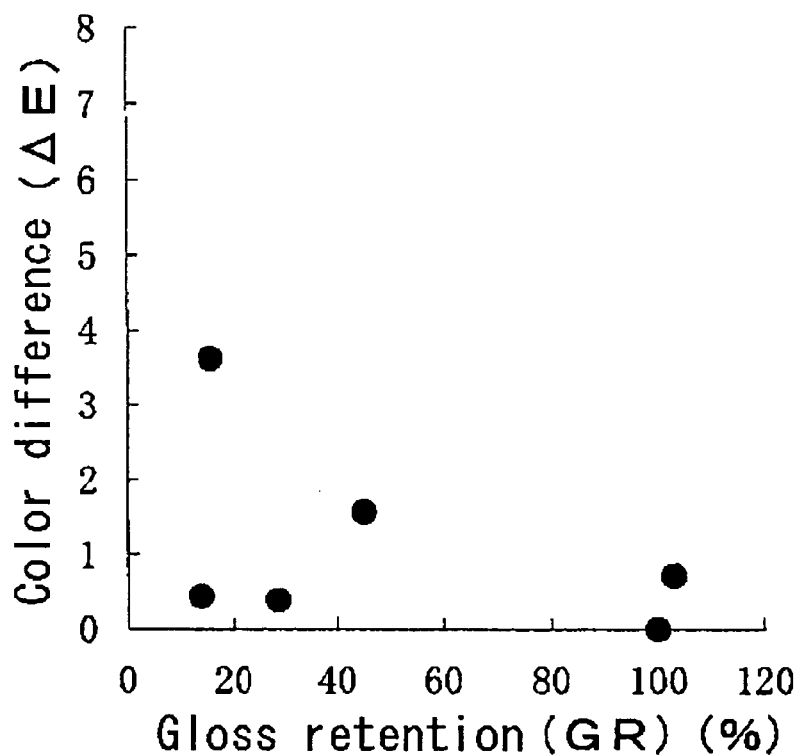
FIG. 22 is a view showing a relationship between gloss retention (GR) and color difference (ΔE) in conducting an accelerated weathering test according to Comparative Example 1 on sample A.
Figure 23:
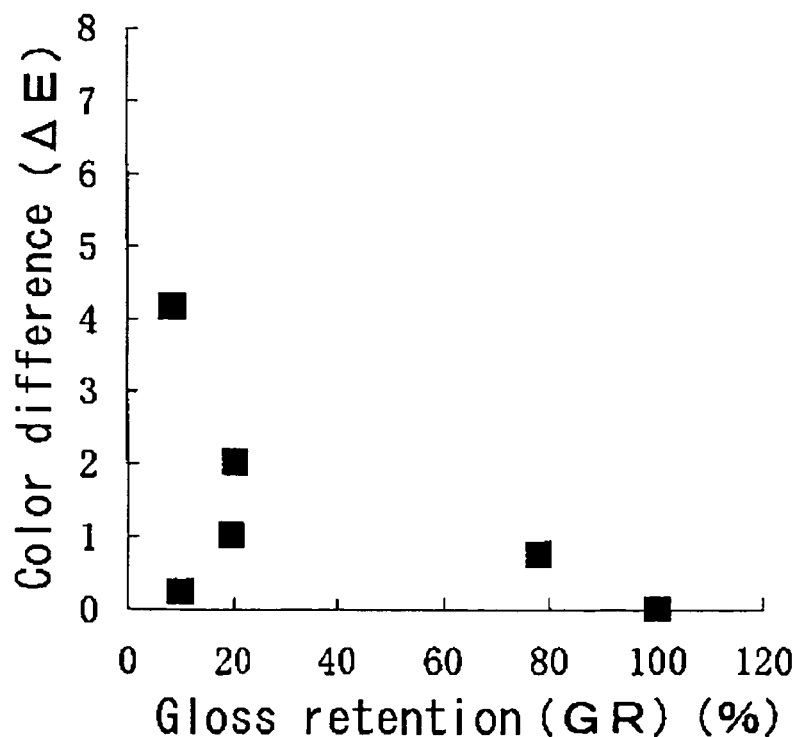
FIG. 23 is a view showing a relationship between gloss retention (GR) and color difference (ΔE) in conducting an accelerated weathering test according to Comparative Example 1 on sample B.
Figure 24:
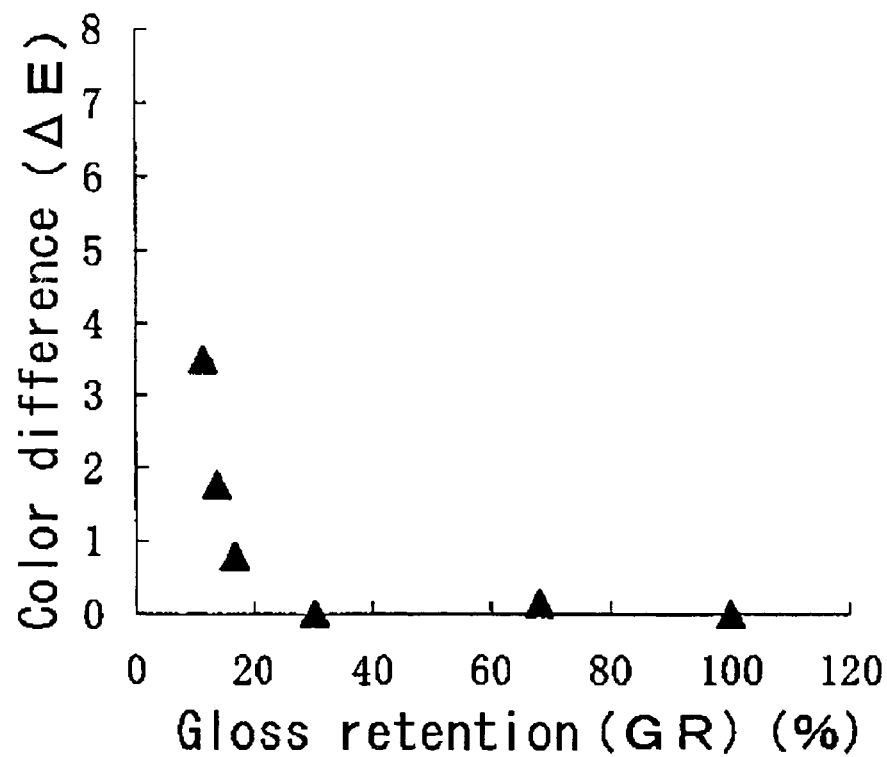
FIG. 24 is a view showing a relationship between gloss retention (GR) and color difference (ΔE) in conducting an accelerated weathering test according to Comparative Example 1 on sample C.
Figure 25:
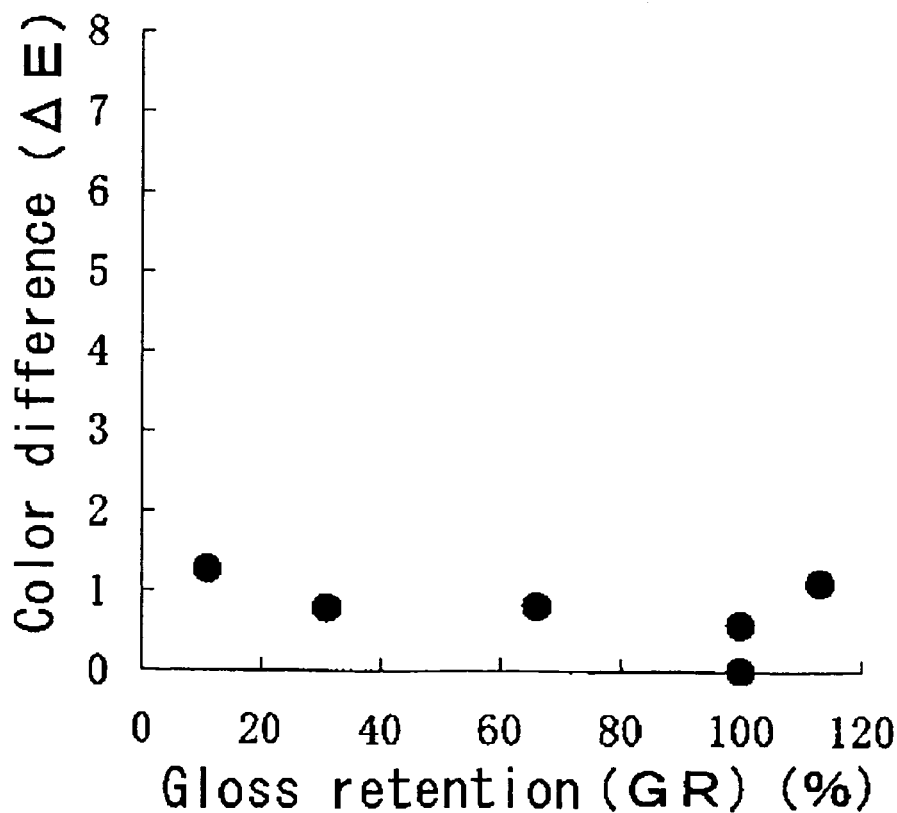
FIG. 25 is a view showing a relationship between gloss retention (GR) and color difference (ΔE) in conducting an accelerated weathering test according to Comparative Example 2 on sample A.
Figure 26:
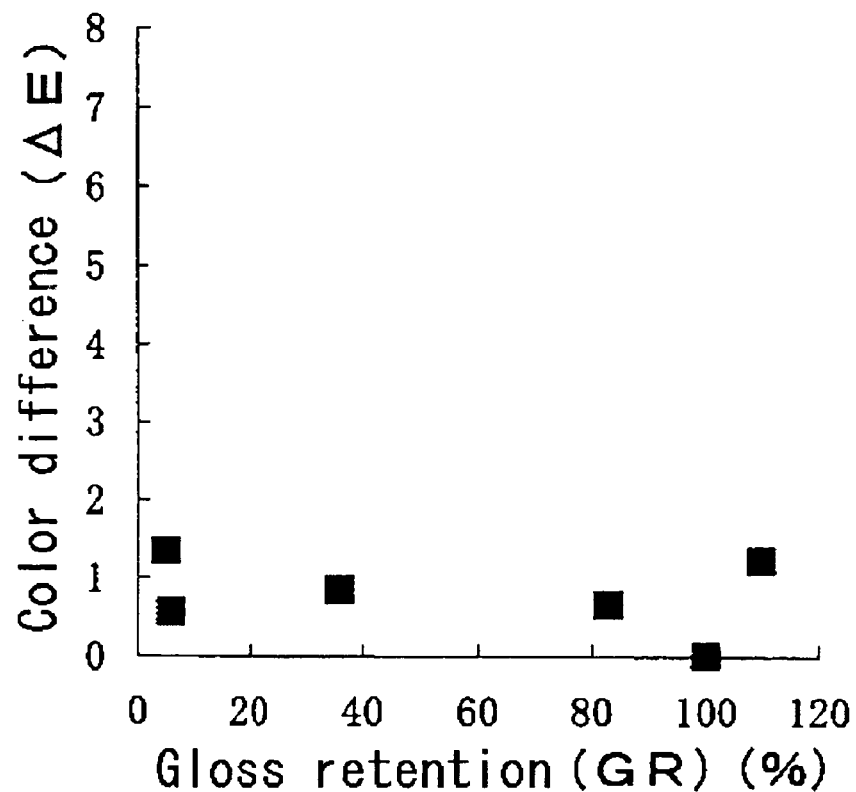
FIG. 26 is a view showing a relationship between gloss retention (GR) and color difference (ΔE) in conducting an accelerated weathering test according to Comparative Example 2 on sample B.
Figure 27:
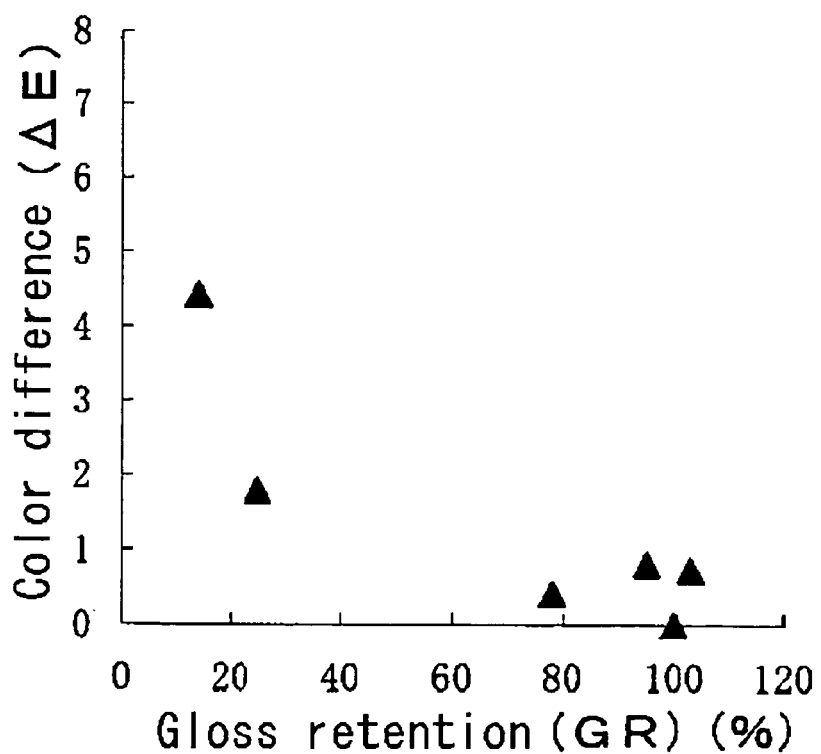
FIG. 27 is a view showing a relationship between gloss retention (GR) and color difference (ΔE) in conducting an accelerated weathering test according to Comparative Example 2 on sample C.
Figure 28:
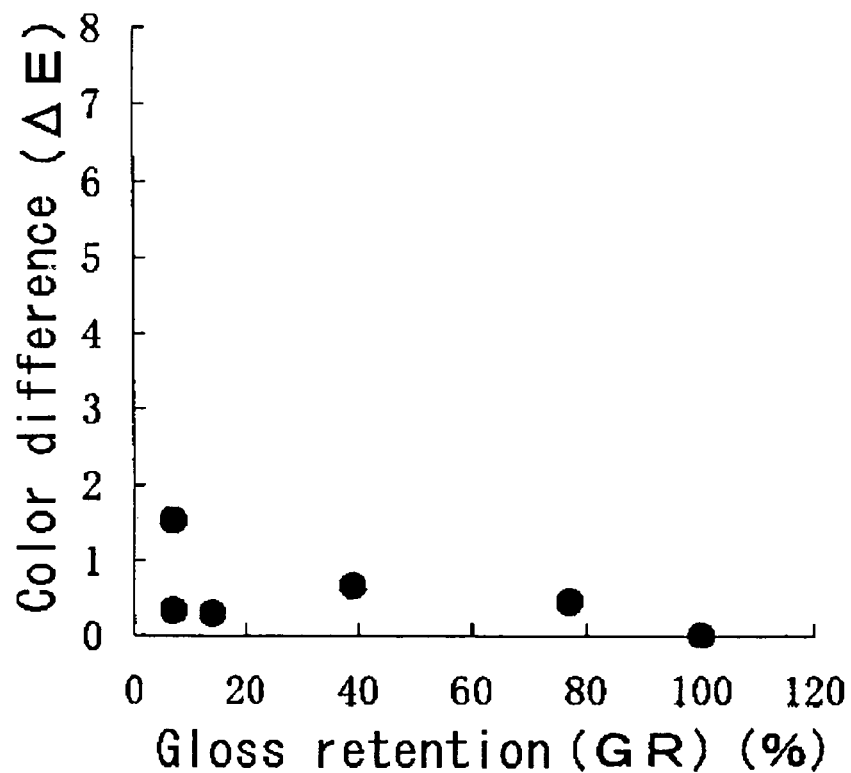
FIG. 28 is a view showing a relationship between gloss retention (GR) and color difference (ΔE) in conducting an accelerated weathering test according to Comparative Example 3 on sample A.
Figure 29:
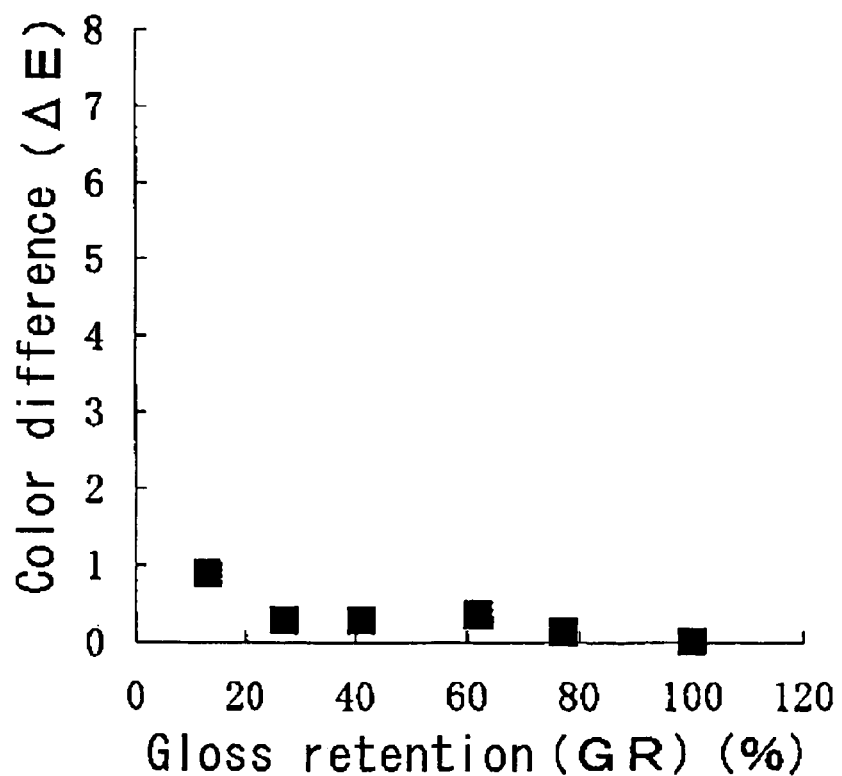
FIG. 29 is a view showing a relationship between gloss retention (GR) and color difference (ΔE) in conducting an accelerated weathering test according to Comparative Example 3 on sample B.
Figure 30:
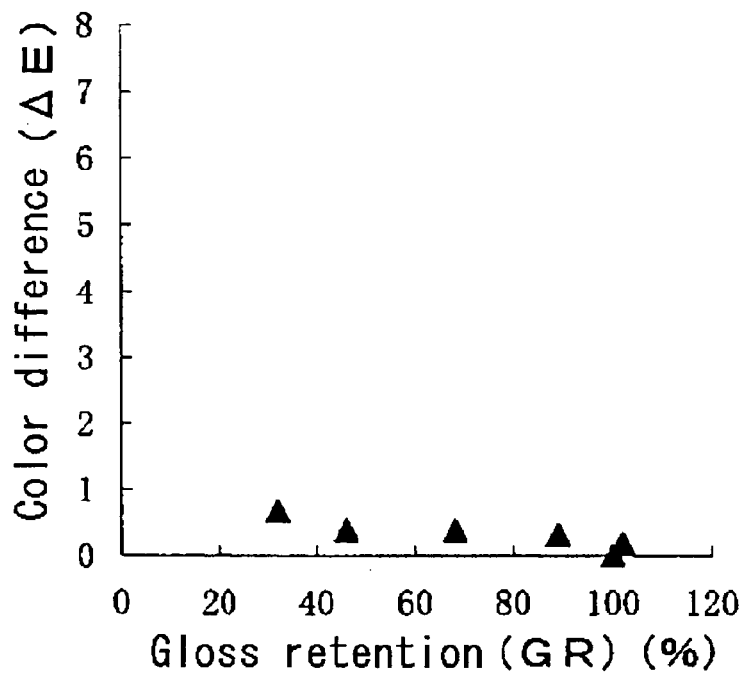
FIG. 30 is a view showing a relationship between gloss retention (GR) and color difference (ΔE) in conducting an accelerated weathering test according to Comparative Example 3 on sample C.

The present inventors have found that the relationships between the gloss retention and the color difference in the outdoor exposure test exhibit a linear correlation as shown in FIGS. 16 to 18. The correlation between the gloss retention and the color difference was also recognized in the results in Examples shown in FIGS. 19 to 21. The correlations in the outdoor exposure test were shown in Table 4 and the correlations in Example were shown in Table 5.

TABLE 4

| Sample | Approximate expression | Coefficient of correlation ($R^2$) |
|---|---|---|
| Sample A | $\Delta E = -0.068GR + 4.97$ | 0.844 |
| Sample B | $\Delta E = -0.081GR + 5.61$ | 0.829 |
| Sample C | $\Delta E = -0.115GR + 7.31$ | 0.876 |

TABLE 5

| Sample | Approximate expression | Coefficient of correlation ($R^2$) |
|---|---|---|
| Sample A | $\Delta E = -0.027GR + 2.80$ | 0.981 |
| Sample B | $\Delta E = -0.037GR + 3.85$ | 0.958 |
| Sample C | $\Delta E = -0.047GR + 4.58$ | 0.964 |

On the other hand, as shown in FIGS. 22 to 30, respectively, the above-mentioned correlation was not recognized in Comparative Examples according to the conventional accelerated weathering test.

Invention 2

(Preparation of Sample)

Each of aqueous acrylic emulsion coating compositions A, B and C, which contains titanium oxide and barium sulfate in the proportions to be 23% as the total PWC and was toned in ivory similarly, was applied to a flat board cut in a predetermined size, on which an under layer comprising an impregnated sealer and a permeance resistant sealer was formed, at a rate of 100 g/m² using a spray. This was set for 5 minutes and then dried at 100° C. for 5 minutes to obtain a sample A, B or C, being an article to be treated, on the surface of which a coating film is formed (Outdoor Exposure Test)

Weathering test by outdoor exposure test was conducted on the above-mentioned samples according to direct exposure tests (JIS Z 2381 General requirements for outdoor exposure test, and JIS K 5600-7-6) at the Okinawa No.2 exposure field of Nippon Paint Co., Ltd. during from September 1994 to September 1999. The location of the exposure field is as follows.

Location: about 26° 20' north latitude and about 127° 45' minutes east longitude Address: 373-309, Kadena-cho Aza Mizugama, Nakagami-gun, Okinawa prefecture In the above-mentioned test, the surface after a lapse of five years was photographed with an electron microscope. The result was shown in FIG. 2. From this picture, it is obvious that the degradation of the surface layer occurs.

(Accelerated Weathering Test Method with a Conventional Apparatus)

An accelerated weathering test was conducted on the above samples A to C referring to JIS K 5400 9.8 (Accelerated weathering) using Daipla Metal Weather (hereinafter, referred to as DMW), which is an accelerated weathering tester of the metal halide lamp type, manufactured by DAIPLA WINTES CO., LTD. In the test, light irradiation of 4 hours was conducted using a light source of 60 mW/cm$_2$ under the conditions of temperature of 63° C. and humidity of 40%, and then after carrying out showering for 10 seconds, the samples were held for 4 hours under the wet conditions of temperature of 30° C. and humidity of 98%. This procedure was takes as one cycle and this cycle was repeated during a predetermined duration. The surface of the coating film after the irradiation of 256 hours was photographed with an electron microscope. The result was shown in FIG. 3. From FIG. 3, it is obvious that not only the degradation of the surface layer but also the degradation of the deep layer occur in the accelerated degradation test method with the conventional apparatus.

(Accelerated Weathering Test Method by Irradiating an Oxygen Atom Converted to a Radical to an Article to be Treated)

A sample was placed on a sample stage 3 in a remote plasma apparatus having a structure illustrated in FIG. 5, and an interior of the apparatus was brought into a reduced pressure by using a vacuum pump 4. Then, an oxygen gas was continued to be flown at a constant flow rate in the direction of the arrow 5. Plasma was generated by using a high-frequency power source 2 (13.56 MHz) and the generated oxygen atom converted to a radical was irradiated to the sample.

EXAMPLE 2 AND COMPARATIVE EXAMPLE

In the apparatus, there were measured temperature rises (° C.) of samples in setting a high-frequency power of a high-frequency power source 2 (13.56 MHz) at 25 W, 50 W, 100 W and 300 W and a degree of vacuum at 0.4 torr, 0.6 torr, 0.8 torr and 1.0 torr taking an oxygen flow rate as 350 ml/min, a distance between a plasma generation section 1 and a sample stage 3 as 150 mm and an irradiation time as 60 minutes. The results were shown in FIG. 31.

Figure 31:
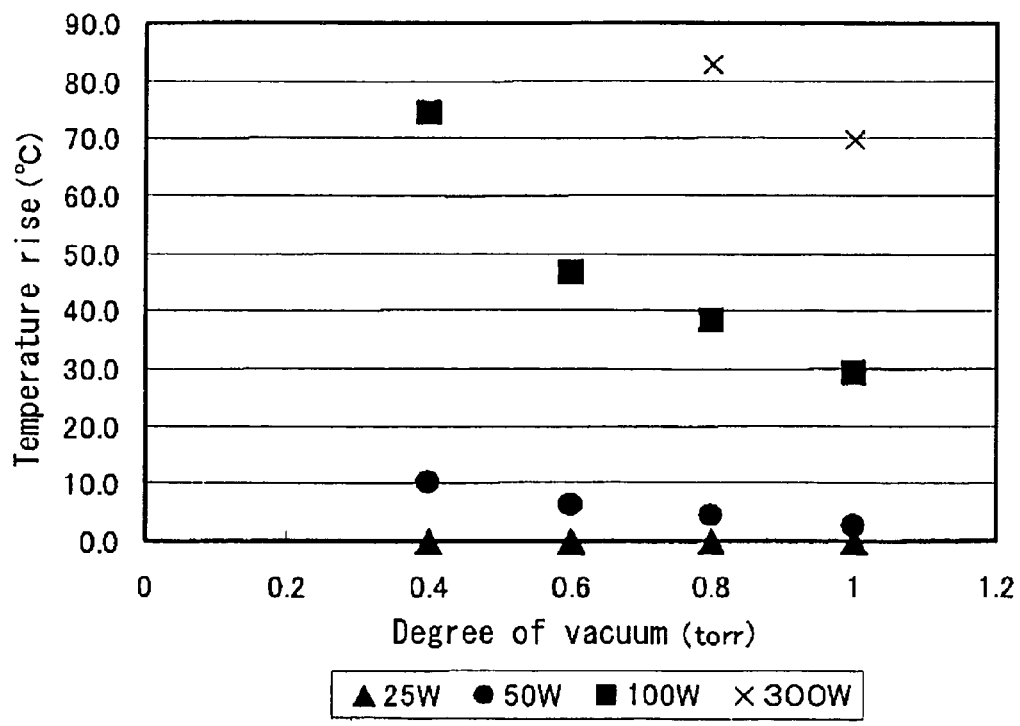
FIG. 31 is a view showing a relationship between a degree of vacuum and a surface temperature rise at respective outputs.

It was found from FIG. 31 that in the case where the degree of vacuum was 0.4 torr, the temperature rises of some samples were found. In the case where the high-frequency power was 300 W, the temperature rises of the samples were noticeable even though the degree of vacuum were 0.8 torr and 1.0 torr.

(Surface Temperature Rise at Respective Outputs at an Irradiation Distance of 350 mm)

In the apparatus, there were measured temperature rises (° C.) of samples in setting a high-frequency power of a high-frequency power source 2 (13.56 MHz) at 50 W, 100 W and 300 W taking an oxygen flow rate as 350 ml/min, a degree of vacuum as 1.0 torr and a distance between a plasma generation section 1 and a sample stage 3 as 350 mm. Relationships between the irradiation time of radical and the temperature rise were shown in FIG. 32.

Figure 32:
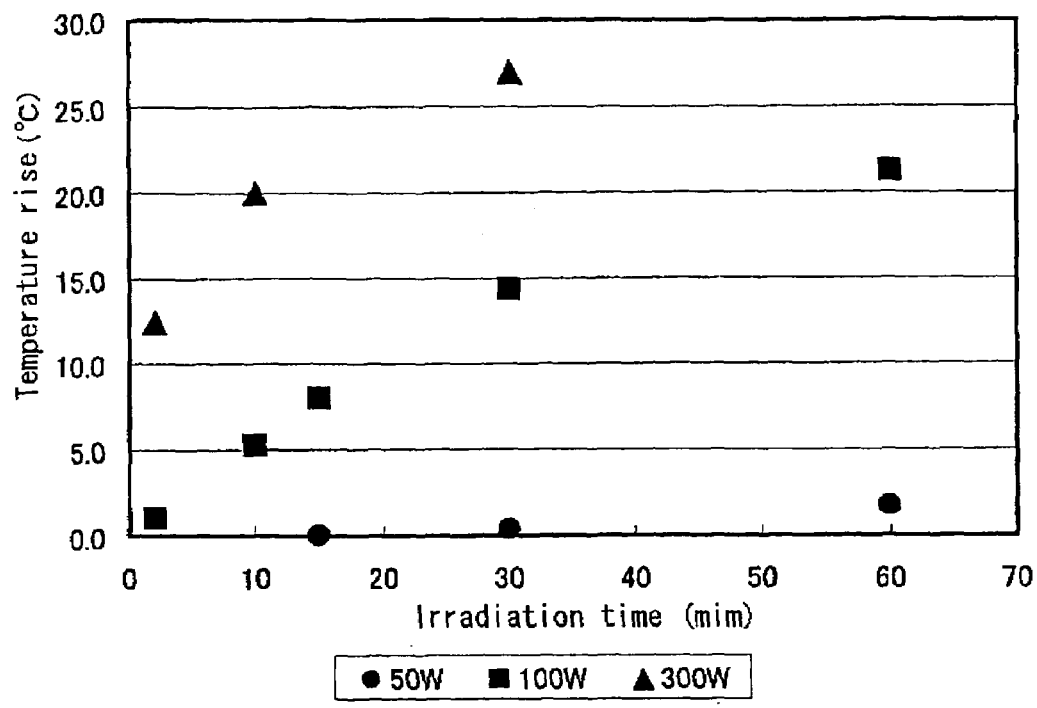
FIG. 32 is a view representing a surface temperature rise at respective outputs at an irradiation distance of 350 mm.

FIG. 32 showed that in the case where the high-frequency power was 100 W or 300 W, the temperature rises of the samples were noticeable because of the high output of the high-frequency power even though the irradiation distance was set at 350 mm.

(Surface Temperature Rise at Respective Outputs at an Irradiation Distance of 150 mm)

In the apparatus, there were measured temperature rises (° C.) of samples in setting a high-frequency power of a high-frequency power source 2 (13.56 MHz) at 50 W, 100 W, 300 W and 600 W taking an oxygen flow rate as 350 ml/min, a degree of vacuum as 1.0 torr and a distance between a plasma generation section 1 and a sample stage 3 as 150 mm. Relationships between the irradiation time of radical and the temperature rise were shown in FIG. 33.

Figure 33:
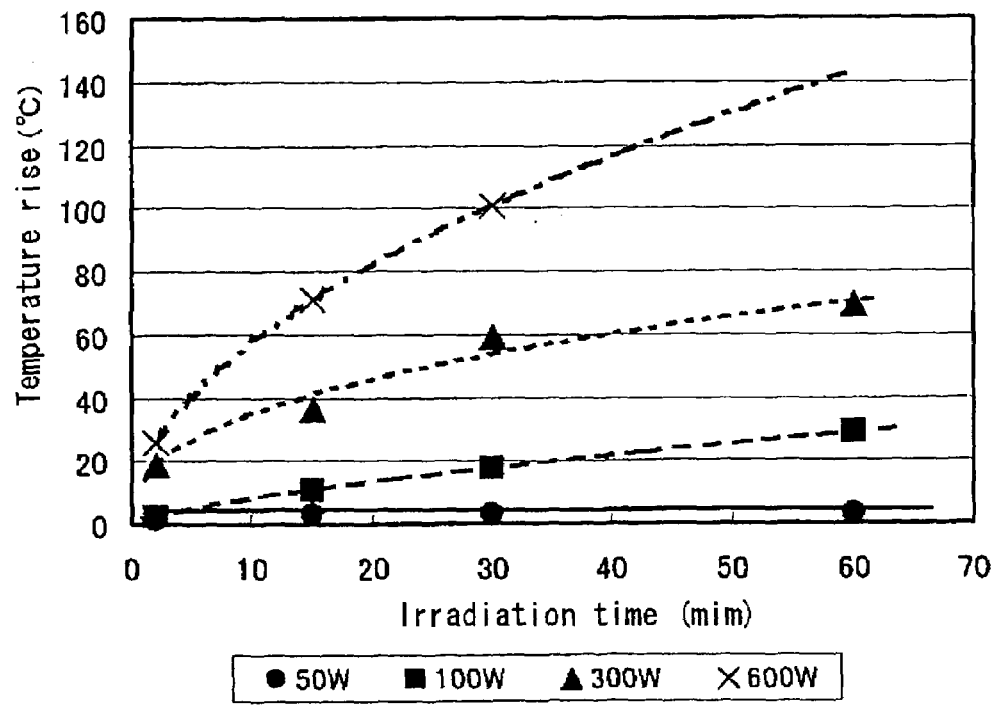
FIG. 33 is a view representing a surface temperature rise at respective outputs at an irradiation distance of 150 mm.

FIG. 33 showed that in the case where the high-frequency power was 300 W or 600 W, the temperature rise of the sample was noticeable. Therefore, the degradation is developed and it is impossible to selectively develop only the degradation of the surface layer.

(Color Difference at Respective Outputs at an Irradiation Distance of 150 mm)

Figure 34:
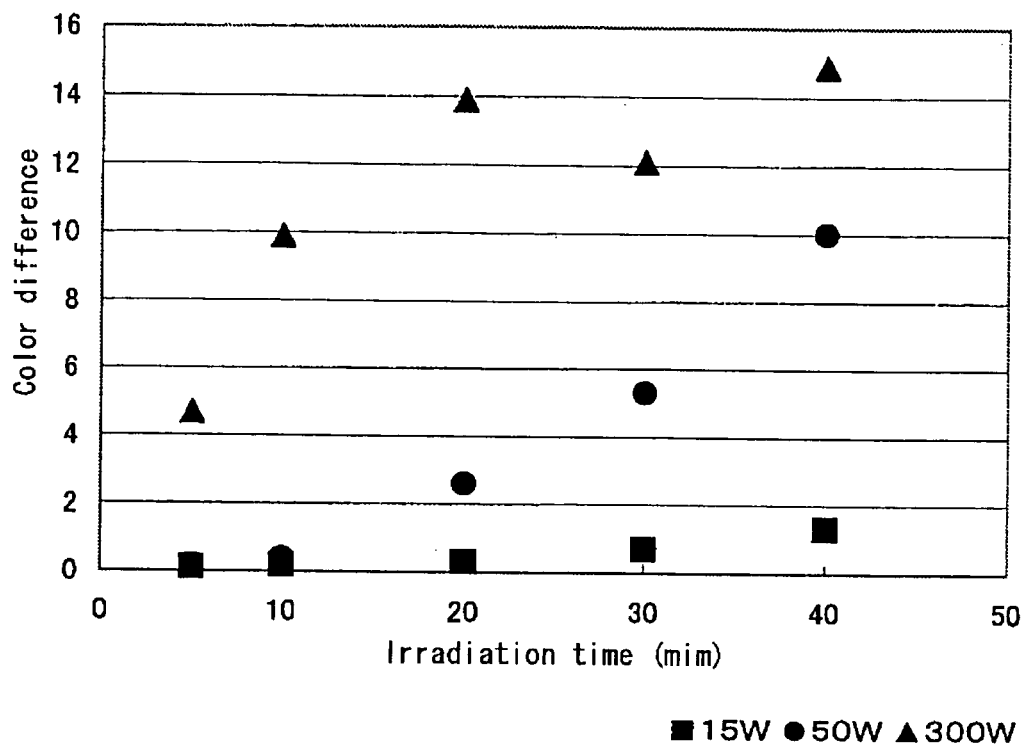
FIG. 34 is a view representing the secular change of color difference at respective outputs.

In the remote plasma apparatus illustrated in FIG. 5, there was measured the secular change of color difference in setting a high-frequency power of a high-frequency power source 2 (13.56 MHz) at 15 W, 50 W and 300 W taking an oxygen flow rate as 350 ml/min, a degree of vacuum as 1.0 torr and a distance between a plasma generation section 1 and a sample stage 3 as 150 mm. Relationships between the irradiation time of radical and the color difference are shown in FIG. 34. In addition, the color difference was measured with a calorimeter CR-300 manufactured by KONICA MINOLTA HOLDINGS, INC.

It was found from FIG. 34 that in the case where the output of a high-frequency power source is 300 W, since the color difference increases rapidly even though the irradiation time is short, a measurement error tends to be large, and therefore it becomes difficult to predict the degradation state of the coating film exactly. And, the color difference hardly changes and an effect of accelerated degradation is very poor in the case where the output of a high-frequency power source is 15 W.

(Change in Color Difference Based on the Difference in an Oxygen Flow Rate)

In the remote plasma apparatus illustrated in FIG. 5, there was measured the secular change of color difference in setting an oxygen flow rate at 30 ml/min, 350 ml/min and 600 ml/min taking a degree of vacuum as 1.0 torr, a distance between a plasma generation section 1 and a sample stage 3 as 150 mm and an output of a high-frequency power source (13.56 MHz) as 50 W. Relationships between the irradiation time of radical and the color difference are shown in FIG. 35.

Figure 35:
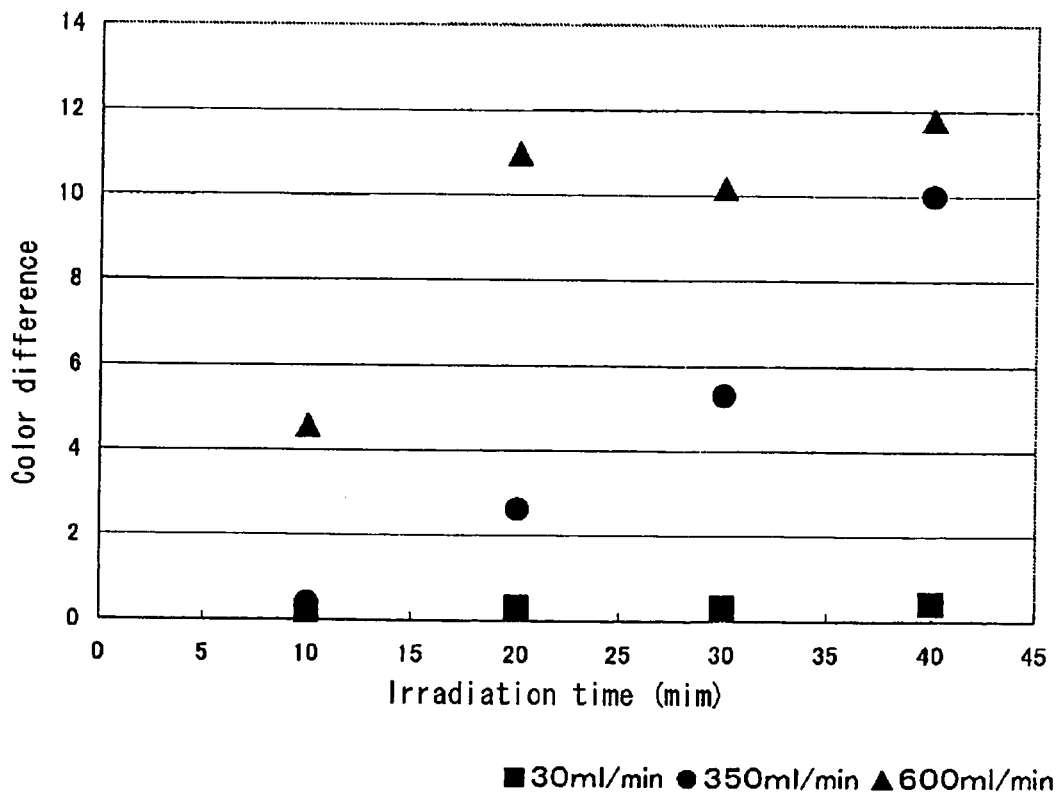
FIG. 35 is a view representing the secular change of color difference at respective oxygen flow rates.

It was found from FIG. 35 that in the case where the oxygen flow rate is 600 ml/min, since the color difference increases rapidly even though the irradiation time is short, a measurement error tends to be large, and therefore it becomes difficult to predict the degradation state of the coating film exactly. And, a speed of the accelerated degradation is slow in the case where the oxygen flow rate is 30 ml/min.

(Change in Color Difference Based on the Difference in a Degree of Vacuum)

In the remote plasma apparatus illustrated in FIG. 5, there was measured the secular change of color difference in setting a degree of vacuum at 0.3 torr, 1.0 torr and 12.0 torr taking an oxygen flow rate as 350 ml/min, a distance between a plasma generation section 1 and a sample stage 3 as 150 mm and an output of a high-frequency power source (13.56 MHz) as 50 W. Relationships between the irradiation time of radical and the color difference are shown in FIG. 36.

Figure 36:
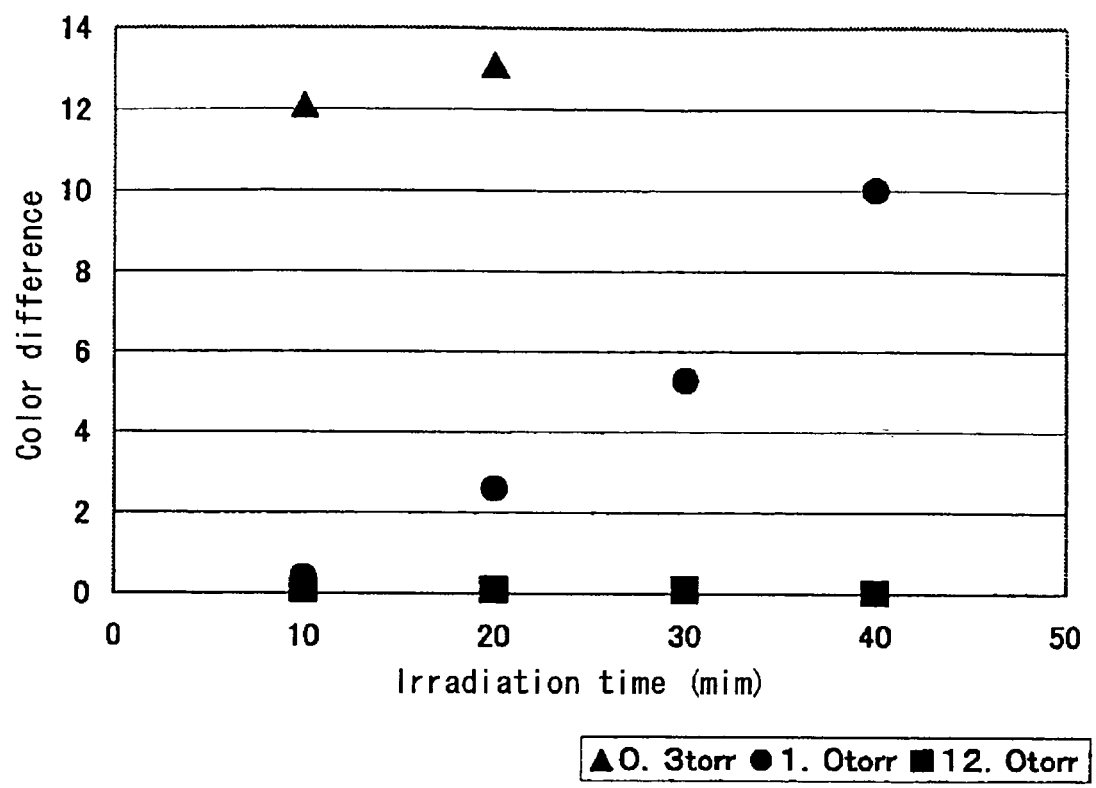
FIG. 36 is a view representing the secular change of color difference at respective degrees of vacuum.

It was found from FIG. 36 that in the case where the degree of vacuum is 0.3 torr, since the color difference increases rapidly even though the irradiation time is short, a measurement error tends to be large, and therefore it becomes difficult to predict the degradation state of the coating film exactly. And, a speed of the accelerated degradation is slow in the case where the degree of vacuum is 12.0 torr.

(Change in Color Difference Based on the Difference in an Amount of Titanium Oxide)

On the three species of coating films, in which the contents of titanium oxide are 16.7 weight %, 44.4 weight % and 72.2 weight %, respectively, the outdoor exposure test was conducted at the conditions described above for 5 years in Okinawa, and the above-mentioned oxygen radical irradiation of 50 minutes, was conducted with a distance between a plasma generation section and a sample stage being 150 mm under the conditions of an oxygen flow rate of 400 ml/min and a degree of vacuum of 1.2 torr using the above-mentioned remote plasma apparatus and the high-frequency power source (13.56 MHz) of 50 W. And, as the conventional accelerated weathering test method, an accelerated weathering test was conducted on the above samples referring to JIS K 5400 9.8 (Accelerated weathering) using Super UV Tester (hereinafter, referred to as SUV), which is an accelerated weathering tester of the metal halide lamp type, manufactured by IWASAKI ELECTRIC Co., Ltd. In the test, light irradiation of 4 hours was conducted using a light source of 100 mW/cm$^2$ under the conditions of temperature of 63° C. and humidity of 40%, and then after carrying out showering for 10 seconds, the samples were held for 4 hours under the wet conditions of temperature of 30° C. and humidity of 98%. This procedure was takes as one cycle and this cycle was repeated during 1200 hours. Each color difference of degraded coating films was measured. The results of measurement are shown in FIG. 4.

As is apparent from FIG. 4, the test results obtained by the accelerated weathering test method of the present invention shows that the color difference increases as the titanium oxide content increases as with the test results obtained by the natural exposure, but the accelerated weathering test with SUV shows the adverse results. From this result, it becomes apparent that the accelerated weathering test method of the present invention gives the results having a high correlation with the results of natural exposure.

INDUSTRIAL APPLICABILITY

In accordance with the present invention, it is possible to provide the accelerated weathering test method, which gives the results having a high correlation with the results of natural exposure and can significantly reduce a test duration.

By the way, this application is a patent application concerning the results of researches commissioned from the nation [commissioned research concerning "Development in resources recycling type coating composition having a high durability and coating system for technical development of next generation housing (limited to concerning resources recycling type housing technical development)" of Ministry of Economy, Trade and Industry, subject to applications of Article 30 of Special measures law on Industrial vitality reproduction].

The invention claimed is:

1. An accelerated weathering test method of accelerating the degradation of the surface of an article to be treated by irradiating plasma to said article to be treated,
wherein said plasma is generated by a remote plasma, said accelerated weathering test method being performed with a selective irradiation of a neutral radical, said irradiation being conducted under the conditions of reduced pressure and a gas flow, and said radical being generated by a remote plasma apparatus using a power source of 20 to 200 W.

2. The accelerated weathering test method according to claim 1, wherein the article to be treated is one having a surface on which a coating film is formed.

3. The accelerated weathering test method according to claim 1, wherein the gas is an oxygen gas.

4. The accelerated weathering test method according to claim 1,
wherein said irradiation is conducted under the conditions of a degree of vacuum of 0.4 to 10 torr and an oxygen flow rate of 50 to 500 ml/min.

5. The accelerated weathering test method according to claim 1,
wherein the accelerated weathering test method is a method of developing selectively the degradation of the surface layer of the article to be treated.

6. The accelerated weathering test method according to claim 1,
wherein a filter is installed between a plasma generation section and a radical irradiation section in order to selectively irradiate the oxygen atom converted to a radical from the remote plasma apparatus.

7. The accelerated weathering test method according to claim 4,
wherein the article to be treated is one having a surface on which a coating film is formed.

8. The accelerated weathering test method according to claim 2,
wherein gas is introduced into the remote plasma apparatus.

9. The accelerated weathering test method according to claim 2,
wherein the accelerated weathering test method is a method of developing selectively the degradation of the surface layer of the article to be treated.

10. The accelerated weathering test method according to claim 1,
wherein a filter is installed between a plasma generation section and a radical irradiation section in order to selectively irradiate the oxygen atom converted to a radical from the remote plasma apparatus.

11. The accelerated weathering test method according to claim 4,
wherein the article to be treated is one having a surface on which a coating film is formed.

12. The accelerated weathering test method according to claim 5,
wherein the article to be treated is one having a surface on which a coating film is formed.

13. The accelerated weathering test method according to claim 6,
wherein the article to be treated is one having a surface on which a coating film is formed.

14. The accelerated weathering test method according to claim 1,
wherein the accelerated weathering test is performed under the condition of keeping the temperature of the article to be treated below 50° C.

15. The accelerated weathering test method according to claim 1,
wherein the accelerated weathering test is performed under the condition of keeping the temperature of the article to be treated below 40° C.

16. The accelerated weathering test method according to claim 1,
wherein the accelerated weathering test is performed wherein the temperature differential of the article to be treated is 3° C.

17. The accelerated weathering test method according to claim 1,
wherein the accelerated weathering test is performed wherein the apparatus has a plasma generation section and a plasma irradiation section and the distance between the plasma generation section and the plasma irradiation section of 20 to 60 cm.

18. The accelerated weathering test method according to claim 1,
wherein the accelerated weathering test is performed with a remote plasma apparatus wherein the apparatus has a plasma generation section and a plasma irradiation section and the distance between the plasma generation section and the plasma irradiation section is adjustable from 20 to 60 cm.

* * * * *